US012758137B2

(12) United States Patent
Beshiri et al.

(10) Patent No.: US 12,758,137 B2
(45) Date of Patent: *Oct. 13, 2026

(54) DECISION TREE BASED SYSTEMS AND METHODS FOR ESTIMATING THE RISK OF ACUTE CORONARY SYNDROME

(71) Applicant: Abbott Laboratories, Abbott Park, IL (US)

(72) Inventors: Agim Beshiri, Abbott Park, IL (US); Shaoqing Du, Abbott Park, IL (US); Janel Huang, Abbott Park, IL (US); Shihai Lu, Abbott Park, IL (US)

(73) Assignee: Abbott Laboratories, Abbott Park, IL (US)

( * ) Notice: Subject to any disclaimer, the term of this patent is extended or adjusted under 35 U.S.C. 154(b) by 1193 days.

This patent is subject to a terminal disclaimer.

(21) Appl. No.: 17/398,589

(22) Filed: Aug. 10, 2021

(65) Prior Publication Data

US 2022/0202342 A1 Jun. 30, 2022

Related U.S. Application Data

(63) Continuation of application No. 15/476,560, filed on Mar. 31, 2017, now Pat. No. 11,147,498.

(60) Provisional application No. 62/343,606, filed on May 31, 2016, provisional application No. 62/316,037, filed on Mar. 31, 2016.

(51) Int. Cl.

| | |
|---|---|
| ***A61B 5/349*** | (2021.01) |
| ***A61B 5/00*** | (2006.01) |
| ***A61B 5/318*** | (2021.01) |
| ***A61B 5/33*** | (2021.01) |
| ***G01N 33/68*** | (2006.01) |
| ***G06F 16/31*** | (2019.01) |
| ***G16H 50/30*** | (2018.01) |
| ***G16H 50/50*** | (2018.01) |

(52) U.S. Cl.

CPC ................ *A61B 5/349* (2021.01); *A61B 5/33* (2021.01); *G01N 33/6887* (2013.01); *G06F 16/322* (2019.01); *G16H 50/30* (2018.01); *G16H 50/50* (2018.01); *A61B 5/7267* (2013.01); *G01N 2333/4712* (2013.01); *G01N 2800/324* (2013.01); *G01N 2800/50* (2013.01); *G01N 2800/56* (2013.01)

(58) Field of Classification Search

None

See application file for complete search history.

(56) References Cited

U.S. PATENT DOCUMENTS

| | | | |
|---|---|---|---|
| 6,099,469 | A | 8/2000 | Armstrong et al. |
| 6,560,541 | B1 | 5/2003 | Singh |
| 8,535,895 | B2 | 9/2013 | Goix et al. |
| 2009/0233312 | A1 | 9/2009 | Gibbons et al. |
| 2009/0312952 | A1 | 12/2009 | Kiefer et al. |
| 2011/0144914 | A1 | 6/2011 | Harrington et al. |
| 2011/0307426 | A1 | 12/2011 | Syed et al. |
| 2012/0076803 | A1 | 3/2012 | Brophy et al. |
| 2012/0264138 | A1 | 10/2012 | Hess et al. |
| 2013/0035603 | A1 | 2/2013 | Jarausch et al. |
| 2016/0091499 | A1 | 3/2016 | Sterling et al. |
| 2017/0296085 | A1 | 10/2017 | Beshiri et al. |

FOREIGN PATENT DOCUMENTS

| | | | |
|---|---|---|---|
| EP | 2554995 | A1 | 2/2013 |
| JP | 2013513387 | A | 4/2013 |
| WO | WO 2009109982 | A1 | 9/2009 |
| WO | WO 2017173353 | A1 | 10/2017 |
| WO | 2022043229 | A1 | 3/2022 |

OTHER PUBLICATIONS

Than Martin P. et al: "Machine Learning to Predict the Likelihood of Acute Myocardial Infarction", Circulation, [Online] vol. 140, No. 11, Aug. 16, 2019 (Aug. 16, 2019), pp. 899-909, XP055981452, US ISSN: 0009-7322, DOI: 10.1161/CIRCULATIONARA.119.041980 Retrieved from the Internet: URL:https://www.ncbi.nlm.nih.gov/pmc/articles/PMC6749969/pdf/cir-140-899.pdf>.

European Patent Office, European Search Report for EP Application No. EP 23201263.3, mailed Feb. 27, 2024.

2010 National Ambulatory Medical Care Survey (NAMCS), 33 pages.

Abe et al., "Early assessment of reperfusion therapy using cardiac troponin T." J Am Coll Cardiol. May 1994;23(6):1382-9.

Apple et al., "Cardiac Troponin Assays: Guide to Understanding Analytical Characteristics and Their Impact on Clinical Care." Clin Chem. Jan. 2017;63(1):73-81.

Apple et al., "Determination of 19 cardiac troponin I and T assay 99th percentile values from a common presumably healthy population." Clin Chem. Nov. 2012;58(11):1574-81.

Aw et al., "Measurement of cardiac troponin I in serum with a new high-sensitivity assay in a large multi-ethnic Asian cohort and the impact of gender." Clin Chim Acta. Jun. 25, 2013;422:26-8.

Backus et al., "A prospective validation of the HEART score for chest pain patients at the emergency department." Int J Cardiol. Oct. 3, 2013;168(3):2153-8.

Bandstein et al., "Undetectable high-sensitivity cardiac troponin T level in the emergency department and risk of myocardial infarction." J Am Coll Cardiol. Jun. 17, 2014;63(23):2569-2578.

(Continued)

*Primary Examiner* — Lori A. Clow

(74) *Attorney, Agent, or Firm* — Lisa Mueller; Casimir Jones SC

(57) ABSTRACT

The invention provides decision tree based systems and methods for estimating the risk of acute coronary syndrome (ACS) in subjects suspect of having ACS. In particular, systems and methods are provided that employ additive decision tree based algorithms to process a subject's initial cardiac troponin I or T (cTnI or cTnT) concentration, a subject's cTnI or cTnT rate of change, and at least one of the following: the subject's age, the subject's gender, the subject's ECG value, the subject's hematology parameter value, to generate an estimate risk of ACS. Such risk stratification allows, for example, patients to be ruled in or rule out with regard to needing urgent treatment.

16 Claims, 14 Drawing Sheets

(56) References Cited

OTHER PUBLICATIONS

Bashore et al., "2012 American College of Cardiology Foundation/ Society for Cardiovascular Angiography and Interventions expert consensus document on cardiac catheterization laboratory standards update: A report of the American College of Cardiology Foundation Task Force on Expert Consensus documents developed in collaboration with the Society of Thoracic Surgeons and Society for Vascular Medicine." J Am Coll Cardiol. Jun. 12, 2012;59(24):2221-305.
Body et al., "Rapid exclusion of acute myocardial infarction in patients with undetectable troponin using a high-sensitivity assay." J Am Coll Cardiol. Sep. 20, 2011;58(13):1332-9.
Body et al., "The Use of Very Low Concentrations of High-sensitivity Troponin T to Rule Out Acute Myocardial Infarction Using a Single Blood Test." Acad Emerg Med. Sep. 2016;23(9):1004-13.
Body, R, et al., The Manchester Acute Coronary Syndromes (MACS) decision rule for suspected cardiac chest pain: derivation and external validation. Heart. 2014;100:1462-1468.
Body, R, et al., Troponin-only Manchester Acute Coronary Syndromes (T-MACS) decision aid: single biomarker re-derivation and external validation in three cohorts. Emerg Med J. 2017;34:349-356.
Body, R, et al., Feasibility of the Manchester Acute Coronary Syndromes (MACS) decision rule to safely reduce unnecessary hospital admissions: a pilot randomised controlled trial. Emerg Med J. 2017;34:586-592.
Bossuyt et al., "STARD 2015: An Updated List of Essential Items for Reporting Diagnostic Accuracy Studies." Clin Chem. Dec. 2015;61(12):1446-52.
Carlton et al., "Evaluation of High-Sensitivity Cardiac Troponin I Levels in Patients With Suspected Acute Coronary Syndrome." JAMA Cardiol. Jul. 1, 2016;1(4):405-12.
Chapman, AR, et al. Comparison of the efficacy and safety of early rule-out pathways for acute myocardial infarction. Circulation. 2017;135:1586-1596.
Collins et al., "Transparent reporting of a multivariable prediction model for Individual Prognosis or Diagnosis (TRIPOD): the TRIPOD statement." Journal of Clinical Epidemiology 68 (2015) 112-121.
Cullen, L, et al. Improved Assessment of Chest Pain Trial (IMPACT): assessing patients with possible acute coronary syndromes. Med J Aust. 2017;207:195-200.
Eggers, KM, et al., Artificial neural network algorithms for early diagnosis of acute myocardial infarction and prediction of infarct size in chest pain patients. Int J Cardiol. 2007;114:366-374.
European Search Report of related 17776836.3, dated Oct. 17, 2019, 11 pages.
Fesmire "Delta CK-MB outperforms delta troponin I at 2 hours during the ED rule out of acute myocardial infarction." Am J Emerg Med. Jan. 2000;18(1):1-8.
Fesmire et al., "Improving risk stratification in patients with chest pain: the Erlanger HEARTS3 score." Am J Emerg Med. Nov. 2012;30(9):1829-37.
Friedman et al., "Additive logistic regression: a statistical view of boosting." The annals of statistics 2000; 28: 337-407.
Friedman, J.H. Greedy function approximation: a gradient boosting machine. Ann Stats. 2001;29:1189-1232.
Gimenez et al., "One-hour rule-in and rule-out of acute myocardial infarction using high-sensitivity cardiac troponin I." Am J Med. Aug. 2015;128(8):861-870.e4.
Gimenez et al., "Rapid rule out of acute myocardial infarction using undetectable levels of high-sensitivity cardiac troponin." Int J Cardiol. Oct. 9, 2013;168(4):3896-901.
Green, M, et al., Detection of acute coronary syndromes in chest pain patients using neural network ensembles. In: Fonseca J., ed. Second International Conference on Computational Intelligence in Medicine and Healthcare. 2005;182-187.
Greenslade, JH, et al., Validating the Manchester Acute Coronary Syndromes (MACS) and Troponin-only Manchester Acute Coronary Syndromes (T-MACS) rules for the prediction of acute myocardial infarction in patients presenting to the emergency department with chest pain. Emerg Med J. 2017;34:517-523.
Hollander et al., "State-of-the-Art Evaluation of Emergency Department Patients Presenting With Potential Acute Coronary Syndromes." Circulation. Aug. 16, 2016;134(7):547-64.
International Search Report of related PCT/US2017/025526, mailed Jun. 27, 2017, 28 pages.
Krittanawong, C, et al. Artificial intelligence in precision cardiovascular medicine. J Am Coll Cardiol. 2017;69:2657-2664.
Leite et al., "Chest pain in the emergency department: risk stratification with Manchester triage system and HEART score." BMC Cardiovasc Disord. Jun. 11, 2015;15:48.
Li et al., "High-sensitivity cardiac troponin T: A biomarker for the early risk stratification of type-A acute aortic dissection?" Arch Cardiovasc Dis. Mar. 2016;109(3):163-70.
Mueller et al., "Multicenter Evaluation of a 0-Hour/1-Hour Algorithm in the Diagnosis of Myocardial Infarction With High-Sensitivity Cardiac Troponin T." Ann Emerg Med. Jul. 2016;68(1):76-87.
Neumann et al., "Diagnosis of Myocardial Infarction Using a High-Sensitivity Troponin I 1-Hour Algorithm." JAMA Cardiol. Jul. 1, 2016;1(4):397-404.
Obermeyer, Z, et al. Predicting the future: big data, machine learning, and clinical medicine. N Engl J Med. 2016;375:1216-1219.
Parsonage et al., "Validation of NICE diagnostic guidance for rule out of myocardial infarction using high-sensitivity troponin tests." Heart. Aug. 15, 2016;102(16):1279-86.
Pickering, JW, et al. Rapid rule-out of acute myocardial infarction with a single high-sensitivity cardiac troponin T measurement below the limit of detection: a collaborative meta-analysis. Ann Intern Med. 2017;166:715-724.
Pickering et al., "Assessment of the European Society of Cardiology 0-Hour/1-Hour Algorithm to Rule-Out and Rule-In Acute Myocardial Infarction." Circulation. Nov. 15, 2016;134(20):1532-1541.
Pickering et al., "Validation of presentation and 3 h high-sensitivity troponin to rule-in and rule-out acute myocardial infarction." Heart. Aug. 15, 2016;102(16):1270-8.
Pickering "MI3 Type 2 explorations" Mar. 14, 2017, 1-9.
Pickering "MI3 Chronic hs-cTnl elevation explorations" Mar. 14, 2017, 1-6.
Pope et al., "Missed diagnoses of acute cardiac ischemia in the emergency department." N Engl J Med. Apr. 20, 2000;342(16):1163-70.
R Core Team. R: A language and environment for statistical computing. https://www.r-project.org/about.html, retrieved on: Mar. 14, 2018, 2 pages.
Reichlin et al., "Early diagnosis of myocardial infarction with sensitive cardiac troponin assays." N Engl J Med. Aug. 27, 2009;361(9):858-67.
Reichlin et al., "One-hour rule-out and rule-in of acute myocardial infarction using high-sensitivity cardiac troponin T." Arch Intern Med. Sep. 10, 2012;172(16):1211-8.
Reichlin et al., "Prospective validation of a 1-hour algorithm to rule-out and rule-in acute myocardial infarction using a high-sensitivity cardiac troponin T assay." CMAJ. May 19, 2015;187(8):E243-52.
Reichlin et al., "Utility of absolute and relative changes in cardiac troponin concentrations in the early diagnosis of acute myocardial infarction." Circulation. Jul. 12, 2011;124(2):136-45.
Roffi et al., "2015 ESC Guidelines for the management of acute coronary syndromes in patients presenting without persistent ST-segment elevation: Task Force for the Management of Acute Coronary Syndromes in Patients Presenting without Persistent ST-Segment Elevation of the European Society of Cardiology (ESC)." Eur Heart J. Jan. 14, 2016;37(3):267-315.
Roffi et al., "Questions and answers on diagnosis and risk assessment: a companion document of the 2015 ESC Guidelines for the

(56) References Cited

OTHER PUBLICATIONS management of acute coronary syndromes in patients presenting without persistent ST-segment elevation†." Eur Heart J. Aug. 29, 2015. , e15-21.

Rubini, Gimenez M, et al. One-hour rule-in and rule-out of acute myocardial infarction using high-sensitivity cardiac troponin I. Am J Med. 2015;128:861-870.e4.

Rubini, Giménez M, et al. Rapid rule out of acute myocardial infarction using undetectable levels of highsensitivity cardiac troponin. Int J Cardiol. 2013;168:3896-3901.

Sandoval et al., "Rapid Rule-Out of Acute Myocardial Injury Using a Single High-Sensitivity Cardiac Troponin I Measurement." Clin Chem. Jan. 2017;63(1):369-376.

Sandoval, Y, et al. Single high-sensitivity cardiac troponin I to rule out acute myocardial infarction. Am J Med. 2017;130:1076-1083. e1.

Sandoval et al., "Present and Future of Cardiac Troponin in Clinical Practice: A Paradigm Shift to High-Sensitivity Assays." Am J Med. Apr. 2016;129(4):354-65.

Shah et al., "High sensitivity cardiac troponin and the under-diagnosis of myocardial infarction in women: prospective cohort study." BMJ. Jan. 21, 2015;350:g7873. 1-8.

Shah et al., "High-sensitivity cardiac troponin I at presentation in patients with suspected acute coronary syndrome: a cohort study." Lancet. Dec. 19, 2015;386(10012):2481-8.

Six et al., "Chest pain in the emergency room: value of the HEART score." Neth Heart J. Jun. 2008;16(6):191-6.

Than et al., "2-Hour accelerated diagnostic protocol to assess patients with chest pain symptoms using contemporary troponins as the only biomarker: the ADAPT trial." J Am Coll Cardiol. Jun. 5, 2012;59(23):2091-8.

Than et al., "A 2-hour diagnostic protocol for possible cardiac chest pain in the emergency department: a randomized clinical trial." JAMA Intern Med. Jan. 2014;174(1):51-8.

Than et al., "Effectiveness of EDACS Versus ADAPT Accelerated Diagnostic Pathways for Chest Pain: A Pragmatic Randomized Controlled Trial Embedded Within Practice." Ann Emerg Med. Jul. 2016;68(1):93-102e1.

Than et al., "What is an acceptable risk of major adverse cardiac event in chest pain patients soon after discharge from the Emergency Department?: a clinical survey." Int J Cardiol. Jul. 1, 2013;166(3):752-4.

Thelin et al., "Early rule-out of acute coronary syndrome using undetectable levels of high sensitivity troponin T." Eur Heart J Acute Cardiovasc Care. Oct. 2015;4(5):403-9.

Thygesen et al., "Third universal definition of myocardial infarction." Circulation. Oct. 16, 2012;126(16):2020-35.

Thygesen et al., "Universal definition of myocardial infarction." Circulation. Nov. 27, 2007;116(22):2634-53.

Westermann, D, et al. High-sensitivity assays for troponin in patients with cardiac disease. Nat Rev Cardiol. 2017;386:1.

Zhelev et al., "Diagnostic accuracy of single baseline measurement of Elecsys Troponin T high-sensitive assay for diagnosis of acute myocardial infarction in emergency department: systematic review and meta-analysis." BMJ. Jan. 20, 2015;350:h15. p. 1-14.

Jaeger C, et al., One-hour rule-in and rule-out of acute myocardial infarction using high-sensitivity cardiac troponin I. Am Heart J. Jan. 2016;171(1):92-102.e1-5. doi: 10.1016/j.ahj.2015.07.022. Epub Jul. 26, 2015. Abstract only—downloaded from https://pubmed.ncbi.nlm.nih.gov/26699605/, 2 pages.

Recruit Holdings Co., Ltd., Press Release, Japan, Nov. 17, 2015, 3 pages.

Chang-Sik Son, et al. Decision-making model for early diagnosis of congestive heart failure using rough set and decision tree approaches. J Biomed Inform. Oct. 2012;45(5):999-1008. doi: 10.1016/j.jbi.2012.04.013. Epub May 4, 2012. Abstract only, 1 page.

European Patent Office, Transmittal of Third Party Observation for EP Application No. EP20230201263 dated Feb. 3, 2025.

STAT High Sensitive Troponin-I package insert, Architect system, Abbott Laboratories, Sep. 2013, 12 pages.

Jerome Friedman, et al. "Additive logistic regression: a statistical view of boosting (With discussion and a rejoinder by the authors)," The Annals of Statistics, Ann. Statist. 28(2), 337-407, (Apr. 2000).

Fesmire, F., et al., "Improving risk stratification in patients with chest pain: the Erlanger HEARTS3 score." Am J Emerg Med. Nov. 2012;30(9):1829-37. doi: 10.1016/j.ajem.2012.03.017. Epub May 23, 2012. PMID: 22626816.

Eggers KM, et al. Artificial neural network algorithms for early diagnosis of acute myocardial infarction and prediction of infarct size in chest pain patients. Int J Cardiol. Jan. 18, 2007;114(3):366-74. doi: 10.1016/j.ijcard.2005.12.019. Epub Jun. 21, 2006. PMID: 16797088.

Fox, Keith A A et al. "Prediction of risk of death and myocardial infarction in the six months after presentation with acute coronary syndrome: prospective multinational observational study (GRACE)." BMJ (Clinical research ed.) vol. 333, 7578 (2006): 1091. doi:10.1136/bmj.38985.646481.55, 6 pages.

Mahler, Simon A et al. "The HEART Pathway randomized trial: identifying emergency department patients with acute chest pain for early discharge." Circulation. Cardiovascular quality and outcomes vol. 8, 2 (2015): 195-203. doi:10.1161/CIRCOUTCOMES.114.001384.

Mahler SA, et al. Identifying patients for early discharge: performance of decision rules among patients with acute chest pain. Int J Cardiol. Sep. 30, 2013;168(2): 795¬802. doi: 10.1016/j.ijcard.2012.10.010. Epub Oct. 30, 2012. PMID: 23117012; PMCID: PMC3565031.

Hess, Erik P et al. "Development of a clinical prediction rule for 30-day cardiac events in emergency department patients with chest pain and possible acute coronary syndrome." Annals of emergency medicine vol. 59, 2 (2012): 115-125.el doi:10.1016/j.annemergmed.2011.07.026.

Green, Michael et al. "Comparison between neural networks and multiple logistic regression to predict acute coronary syndrome in the emergency room." Artificial intelligence in medicine vol. 38, 3 (2006): 305-318. doi:10.1016/j.artmed.2006.07.006.

Podgorelec, Vili et al. "Decision trees: an overview and their use in medicine." Journal of medical systems vol. 26, 5 (2002): 445-463. doi:10.1023/a:1016409317640.

Agewall, Giannitsis, Jernberg and Katus. "Troponin elevation in coronary vs. non-coronary disease". Frontiers in cardiovascular medicine. European Heart Journal (2011) 32, 404-411.

Wereski, R. et al. "Cardiac Troponin Thresholds and Kinetics to Differentiate Myocardial Injury and Myocardial Infarction". Circulation. 2021;144: 528-538.

Salari, Nader et al. "Application of pattern recognition tools for classifying acute coronary syndrome: an integrated medical modeling." Theoretical biology & medical modelling vol. 10: 57. Sep. 18, 2013, doi:10.1186/1742-4682-10-57, 17 pages.

Breiman, L. Random Forests. Machine Learning 45, 5-32 (2001) https://doi.org/10.1023/A:1010933404324.

Granger, Christopher B et al. "Predictors of hospital mortality in the global registry of acute coronary events." Archives of internal medicine vol. 163, 19 (2003): 2345-2353 doi:10.1001/archinte.163.19.2345.

Neumann, Johannes Tobias et al. "Personalized diagnosis in suspected myocardial infarction". Clinical Research in Cardiology (2023) 112: 1288-1301.

Doudesis, Dimitrios et al. "Machine learning for diagnosis of myocardial infarction using cardiac troponin concentrations". Nature Medicine, vol. 29, May 2023; 1201-1210.

Doudesis Dimitrios et al. "Validation of the myocardial-ischaemic-injury-index machine learning algorithm to guide the diagnosis of myocardial infarction in a heterogeneous population: a prespecified exploratory analysis", The Lancet Digital Health, vol. 4, May 2022, pp. e300.

European Patent Office, Communication of a Notice of Opposition for EP Application No. 17776836.3 mailed Jul. 22, 2024.

FIG. 4

Patient Report

| | |
|---|---|
| First cTnI Result | 9 |
| First Result Time | 12:30:00 PM |
| Second cTnI Result | 11.00 |
| Second Result Time | 3:00:00 PM |
| Gender | Female |
| Age | 44 |

| | |
|---|---|
| Index Value | 2.59 |
| Reference Statistics | |
| Sensitivity | 98.87 [ 96.73, 99.77] |
| Specificity | 66.75 [ 64.44, 69.00] |
| PPV | 31.91 [ 28.73, 35.22] |
| NPV | 99.73 [ 99.22, 99.94] |

| Group | TP | FP | FN | TN |
|---|---|---|---|---|
| **Sex** | | | | |
| Male | 882 | 2642 | 6 | 3310 |
| Female | 362 | 1438 | 3 | 2368 |
| **Age** | | | | |
| <=65 | 546 | 1892 | 6 | 4597 |
| >65 | 698 | 2188 | 3 | 1081 |
| **History of CAD** | | | | |
| TRUE | 534 | 1646 | 4 | 1102 |
| FALSE | 710 | 2434 | 5 | 4576 |
| **History of DM** | | | | |
| TRUE | 294 | 915 | 4 | 717 |
| FALSE | 949 | 3141 | 5 | 4953 |
| **History of HTN** | | | | |
| TRUE | 844 | 2938 | 6 | 2487 |
| FALSE | 395 | 1128 | 3 | 3178 |
| **Current Smoker** | | | | |
| TRUE | 276 | 834 | 3 | 1492 |
| FALSE | 941 | 3211 | 6 | 4135 |
| **Time from symptoms** | | | | |
| <=3h | 370 | 1248 | 0 | 2066 |
| >3h | 840 | 2319 | 6 | 3169 |
| **Primary Outcome** | | | | |
| Overall | 1244 | 4080 | 9 | 5678 |

| Group | TP | FP | FN | TN |
|---|---|---|---|---|
| **Sex** | | | | |
| Male | 626 | 173 | 262 | 5779 |
| Female | 226 | 113 | 139 | 3693 |
| **Age** | | | | |
| <=65 | 376 | 126 | 176 | 6363 |
| >65 | 476 | 160 | 225 | 3109 |
| **History of CAD** | | | | |
| TRUE | 332 | 94 | 206 | 2654 |
| FALSE | 520 | 192 | 195 | 6818 |
| **History of DM** | | | | |
| TRUE | 192 | 58 | 106 | 1574 |
| FALSE | 659 | 227 | 295 | 7867 |
| **History of HTN** | | | | |
| TRUE | 550 | 189 | 300 | 5237 |
| FALSE | 299 | 97 | 99 | 4209 |
| **Current Smoker** | | | | |
| TRUE | 202 | 56 | 77 | 2270 |
| **Primary Outcome** | | | | |
| FALSE | 634 | 227 | 313 | 7119 |
| Overall | 852 | 286 | 401 | 9472 |
| **Time from symptoms** | | | | |
| <=3h | 240 | 108 | 130 | 3226 |
| >3h | 586 | 146 | 260 | 5342 |

| Group | TP | FP | FN | TN |
|---|---|---|---|---|
| **Cohort** | | | | |
| BACC | 125 | 57 | 54 | 1246 |
| HighSTEACS | 147 | 25 | 78 | 1279 |
| UTROPIA | 49 | 69 | 19 | 1494 |
| APACE | 227 | 94 | 103 | 2070 |
| ADAPT-CH | 169 | 7 | 73 | 780 |
| ADAPT-BN | 24 | 10 | 17 | 730 |
| IMPACT | 25 | 10 | 20 | 1044 |
| TIMI RCT | 46 | 9 | 17 | 359 |
| EDACS RCT | 40 | 5 | 20 | 468 |
| **Time between samples** | | | | |
| <1.5h | 169 | 65 | 60 | 1686 |
| 1.5 to <2.5h | 511 | 119 | 229 | 5019 |
| 2.5 to <3.5h | 110 | 61 | 62 | 1719 |
| >=3.5h | 62 | 41 | 30 | 1038 |
| **Time from symptoms*** | | | | |
| <=1 | 21 | 28 | 15 | 968 |
| >1 to <=2 | 79 | 32 | 36 | 1032 |
| >2 to <=3 | 63 | 20 | 29 | 798 |
| >3h | 546 | 120 | 255 | 4989 |

DECISION TREE BASED SYSTEMS AND METHODS FOR ESTIMATING THE RISK OF ACUTE CORONARY SYNDROME

The present application is a continuation of U.S. patent application Ser. No. 15/476,560, filed Mar. 31, 2017, now allowed, which claims priority to U.S. Provisional applications 62/316,037 filed Mar. 31, 2016, and 62/343,606 filed May 31, 2016, each of which are herein incorporated by reference in their entireties.

FIELD OF THE INVENTION

The invention provides decision tree based systems and methods for estimating the risk of acute coronary syndrome (ACS) in subjects suspect of having ACS or an ACS comorbidity. In particular, systems and methods are provided that employ additive decision tree based algorithms to process a subject's initial cardiac troponin I or T (cTnI or cTnT) concentration, a subject's cTnI or cTnT rate of change, and the subject's age, a subject's ECG value, a subject's hematology parameter value, and/or gender to generate an estimate risk of ACS or an ACS comorbidity. Such risk stratification allows, for example, patients to be ruled in or rule out with regard to needing urgent treatment.

BACKGROUND

Suspected ACS patients comprise up to 8 million patients presenting to US emergency departments each year. While up to 20-25% of these patients are having a heart attack, the rest are not. The standard of care currently deals with false positives that are triaged to the cardiac catheterization lab which is not risk free (~1/1000 adverse events, 1/10000 deaths). Additionally, the false negative rate that may result in misdiagnosis leads to more severe outcomes or increased mortality. Lastly healthcare costs are incurred due to the inadequate and untimely stratification of this patient population. The ACS population includes those with ST elevation myocardial infarction (STEMI), non-ST elevation myocardial infarction (NSTEMI) and unstable angina (UA), with the latter two categories containing most of the diagnosed ACS patients. Current guidelines and the standard of care address suspected ACS patients based on clinical presentation, history and physical as well as diagnostic methods such as ECG and Troponin measurements. For STEMI, the ECG is the gold standard in identifying patients with structural damage reflected by ST elevations on the ECG. For NSTEMI and UA troponin measurements are the gold standard in helping stratify these patients into appropriate risk categories for MI and triaging them quickly. Guidelines recommend measuring troponin and comparing to a 99% threshold. However, such comparison is not individualized for a patient's particular characteristics and can lead to false negatives and false positives regarding risk of ACS.

SUMMARY OF THE INVENTION

The invention provides decision tree based systems and methods for estimating the risk of acute coronary syndrome (ACS), and/or an ACS comorbidity, in subjects suspect of having ACS or an ACS comorbidity. In particular, systems and methods are provided that employ additive decision tree based algorithms to process a subject's initial cardiac troponin I or T (cTnI or cTnT) concentration, a subject's cTnI or cTnT rate of change, the subject's age, a subject ECG value, a subject hematology parameter value (e.g., white cell mean volume, platelet population data, and red cell sub-population data, or other complete blood count data generated by a hematology analyzer), and/or gender to generate an estimate risk of ACS, and/or an ACS comorbidity. Such risk stratification allows, for example, patients to be ruled in or rule out with regard to needing urgent treatment.

In some embodiments, provided herein are methods for reporting an estimated risk of acute coronary syndrome (ACS) (e.g., in a subject suspected of having ACS), and/or an ACS comorbidity (e.g., in a subject suspected of having an ACS comorbidity), comprising: a) obtaining subject values for the subject, and wherein the subject values comprise: i) at least one of the following: subject gender value, ECG (electrocardiogram) value, hematology parameter value (e.g., white cell mean volume, platelet population data, and red cell sub-population data, or other complete blood count data generated by a hematology analyzer), and subject age value, ii) subject initial cardiac troponin I and/or T (cTnI or cTnT) concentration from an initial sample from the subject, and iii) a first and/or second subsequent cTnI and/or cTnT concentration from corresponding first and/or second subsequent samples from the subject; b) processing the subject values with a processing system such that an estimated risk of ACS, and/or an ACS comorbidity, is determined for the subject, wherein the processing system comprises: i) a computer processor, and ii) non-transitory computer memory (e.g., single memory component or multiple, distributed memory components) comprising one or more computer programs and a database, wherein the one or more computer programs comprise: a rate of change algorithm and an additive tree algorithm, and wherein the database comprises at least M number of decision trees (e.g., 4 . . . 20 . . . 50 . . . 100 . . . 500 . . . 800 . . . 1000 or more decision trees), wherein each individual decision tree comprises at least two pre-determined splitting variables and at least three pre-determined terminal node values, wherein the at least two pre-determined splitting variables are selected from the group consisting of: a threshold cTnI and/or cTnT rate of change value, a threshold initial cTnI and/or cTnT concentration value, and at least one of the following: a gender value, a threshold ECG value, a threshold hematology parameter value, and an age threshold value, wherein the one or more computer programs, in conjunction with the computer processor, is/are configured to: A) apply the rate of change algorithm to determine a subject cTnI and/or cTnT rate of change value from at least two of: the subject initial cTnI and/or cTnT concentration, the first subsequent cTnI and/or cTnT concentration, and the second subsequent cTnI and/or cTnT concentration, B) apply the subject cTnI and/or cTnT rate of change value, the subject initial cTnI and/or cTnT concentration, and at least one of the following: the subject gender value, the subject ECG value, the subject hematology parameter, and/or the age value to the database to determine a terminal node value for each of the at least M number of decision trees, and C) apply the additive tree algorithm to: I) determine a combined value from M number of the terminal node values, and II) process the combined value to determine an estimated risk of ACS, and/or an ACS comorbidity, for the subject; and c) reporting the estimated risk of ACS, and/or an ACS comorbidity, for the subject determined by the processing system.

In certain embodiments, said process the combined value to determine an estimated risk comprises determining an index value, and comparing said index value to an estimated risk index value look up table to determine the estimated risk. In particular embodiments, the ACS is Type I myocardial infarction, and if the subject's index value is below about 1.1, they are determined to have low risk; if the subject's index value is between about 1.1 and about 57.0, they are determined to be of intermediate risk; and if the subject's value is above about 57.1, they are determined to be high risk. In other embodiments, the ACS is myocardial infarction, and if the subject's index value is equal to or below about 3.0, they are determined to have low risk; if the subject's index value is between about 3.1 and about 48.9, they are determined to be of intermediate risk; and if the subject's value is equal to or above about 49.0, they are determined to be high risk.

In other embodiments, provided herein are methods for reporting an estimated risk of acute coronary syndrome (ACS), and/or an ACS comorbidity, in a subject (e.g., suspected of having ACS or ACS comorbidity) comprising: a) obtaining subject values for the subject, and wherein the subject values comprise: i) at least one of the following: subject gender value (e.g., arbitrary value, where the female value is lower than the male value), subject age value, subject ECG value, and subject hematology parameter value, ii) subject initial cardiac troponin I or T (cTnI or cTnT) concentration from an initial sample from the subject, and iii) a subject cTnI and/or cTnT rate of change value based on at least two samples taken from the subject at different times; b) processing the subject values with a processing system such that an estimated risk of ACS, and/or an ACS comorbidity, is determined for the subject, wherein the processing system comprises: i) a computer processor, and ii) non-transitory computer memory comprising one or more computer programs and a database, wherein the one or more computer programs comprise an additive tree algorithm, and wherein the database comprises at least M number of decision trees, wherein each individual decision tree comprises at least two pre-determined splitting variables and at least three pre-determined terminal node values, wherein the at least two pre-determined splitting variables are selected from the group consisting of: a threshold cTnI and/or cTnT rate of change value, a threshold initial cTnI and/or cTnT concentration value, a gender value, a threshold ECG value, a threshold hematology parameter value, and an age threshold value, wherein the one or more computer programs, in conjunction with the computer processor, is/are configured to: A) apply the subject cTnI and/or cTnT rate of change value, the subject initial cTnI and/or cTnT concentration, and the subject gender value and/or the age value to the database to determine a terminal node value for each of the at least M number of decision trees (e.g., 4 . . . 20 . . . 50 . . . 100 . . . 500 . . . 800 . . . 1000 or more decision trees), and B) apply the additive tree algorithm to: I) determine a combined value from M number of the terminal node values, and II) process the combined value to determine an estimated risk of ACS, and/or an ACS comorbidity, for the subject; and, in certain embodiments further comprising, c) reporting the estimated risk of ACS, and/or an ACS comorbidity, for the subject determined by the processing system.

In certain embodiments, provided herein are processing systems comprising: a) a computer processor, and b) non-transitory computer memory comprising one or more computer programs and a database, wherein the one or more computer programs comprise an additive tree algorithm, and wherein the database comprises at least M number of decision trees (e.g., 4 . . . 20 . . . 50 . . . 100 . . . 500 . . . 800 . . . 1000 or more decision trees), wherein each individual decision tree comprises at least two pre-determined splitting variables and at least three pre-determined terminal node values, wherein the at least two pre-determined splitting variables are selected from the group consisting of: a threshold cTnI and/or cTnT rate of change value, a threshold initial cTnI and/or cTnT concentration value, a gender value, a threshold ECG value, a threshold hematology parameter value, and an age threshold value, wherein the one or more computer programs, in conjunction with the computer processor, is/are configured to: A) apply a subject cTnI and/or cTnT rate of change value, a subject initial cTnI and/or cTnT concentration, and at least one of the following: a subject gender value, a subject age value, a subject ECG value, and a subject hematology parameter value, to the database to determine a terminal node value for each of the at least M number of decision trees (e.g., 4 . . . 20 . . . 50 . . . 100 . . . 500 . . . 800 . . . 1000 or more decision trees), and B) apply the additive tree algorithm to: I) determine a combined value from M number of the terminal node values, and II) process the combined value to determine an estimated risk of ACS, and/or an ACS comorbidity, for the subject. In particular embodiments, the systems further comprise a report that provides the estimated risk of ACS, and/or an ACS comorbidity, for the subject.

In some embodiments, provided herein is a non-transitory computer memory component comprising: one or more computer programs configured to access a database, wherein the one or more computer programs comprise a rate of change algorithm and an additive tree algorithm, and wherein the database comprises at least M number of decision trees (e.g., 4 . . . 20 . . . 50 . . . 100 . . . 500 . . . 800 . . . 1000 or more decision trees), wherein each individual decision tree comprises at least two pre-determined splitting variables and at least three pre-determined terminal node values, wherein the at least two pre-determined splitting variables are selected from the group consisting of: a threshold cTnI and/or cTnT rate of change value, a threshold initial cTnI and/or cTnT concentration value, a gender value, a threshold ECG value, a threshold hematology parameter value, and an age threshold value, wherein the one or more computer programs, in conjunction with the computer processor, is/are configured to: i) apply the rate of change algorithm to determine a subject cTnI and/or cTnT rate of change value from at least two of: a subject initial cTnI and/or cTnT concentration, a first subject subsequent cTnI and/or cTnT concentration, and a second subject subsequent cTnI and/or cTnT concentration, ii) apply the subject cTnI and/or cTnT rate of change value, the subject initial cTnI and/or cTnT concentration, and at least one of the following: a subject gender value, a subject ECG value, a subject hematology parameter value, and an age value to the database to determine a terminal node value for each of the at least M number of decision trees, and iii) apply the additive tree algorithm to: a) determine a combined value from M number of the terminal node values, and b) process the combined value to determine an estimated risk of ACS, and/or an ACS comorbidity, for the subject. In certain embodiments, the non-transitory computer memory component further comprises the database.

In certain embodiments, provided herein is a non-transitory computer memory component comprising: one or more computer programs configured to access a database, wherein the one or more computer programs comprise an additive tree algorithm, and wherein the database comprises at least M number of decision trees (e.g., 4 . . . 20 . . . 50 . . . 100 . . . 500 . . . 800 . . . 1000 or more decision trees), wherein each individual decision tree comprises at least two pre-determined splitting variables and at least three pre-determined terminal node values, wherein the at least two pre-determined splitting variables are selected from the group consisting of: a threshold cTnI and/or cTnT rate of change value, a threshold initial cTnI and/or cTnT concentration value, a threshold ECG value, a threshold hematology parameter, a gender value, and an age threshold value, wherein the one or more computer programs, in conjunction with the computer processor, is/are configured to: A) apply a subject cTnI and/or cTnT rate of change value, a subject initial cTnI and/or cTnT concentration, and at least one of the following: a subject gender value, a subject age value, a subject ECG value, and a subject hematology parameter, to the database to determine a terminal node value for each of the at least M number of decision trees, and B) apply the additive tree algorithm to: I) determine a combined value from M number of the terminal node values, and II) process the combined value to determine an estimated risk of ACS, and/or an ACS comorbidity, for the subject. In certain embodiments, the non-transitory computer memory component further comprises the database.

In some embodiments, provided herein are processing systems comprising: a) a computer processor, and b) non-transitory computer memory comprising one or more computer programs and a database, wherein the one or more computer programs comprise: a rate of change algorithm and an additive tree algorithm, and wherein the database comprises at least M number of decision trees (e.g., 4 . . . 20 . . . 50 . . . 100 . . . 500 . . . 800 . . . 1000 or more decision trees), wherein each individual decision tree comprises at least two pre-determined splitting variables and at least three pre-determined terminal node values, wherein the at least two pre-determined splitting variables are selected from the group consisting of: a threshold cTnI and/or cTnT rate of change value, a threshold initial cTnI and/or cTnT concentration value, a gender value, a ECG threshold value, a hematology parameter threshold value, and an age threshold value, wherein the one or more computer programs, in conjunction with the computer processor, is/are configured to: i) apply the rate of change algorithm to determine a subject cTnI and/or cTnT rate of change value from at least two of: a subject initial cTnI and/or cTnT concentration, a first subject subsequent cTnI and/or cTnT concentration, and a second subject subsequent cTnI and/or cTnT concentration, ii) apply the subject cTnI and/or cTnT rate of change value, the subject initial cTnI and/or cTnT concentration, and at least one of: a subject gender value, a subject ECG value, a subject hematology parameter value, and an age value to the database to determine a terminal node value for each of the at least M number of decision trees, and iii) apply the additive tree algorithm to: a) determine a combined value from M number of the terminal node values, and b) process the combined value to determine an estimated risk of ACS, and/or an ACS comorbidity, for the subject.

In certain embodiments, the systems further comprise a display, wherein the display is operably linked to the non-transitory computer memory and is configured to display the risk of ACS, and/or an ACS comorbidity, for the subject. In further embodiments, the estimated risk of ACS, and/or an ACS comorbidity, for the subject is reported as higher risk (e.g., likely to have ACS, and/or an ACS comorbidity), moderate risk (e.g., unclear if the subject has ACS or ACS comorbidity, so more testing may be needed), or lower risk (e.g., subject is unlikely to have ACS or ACS comorbidity, and therefore does not need any further testing or treatment). In particular embodiments, the estimated risk of ACS, and/or estimated risk of an ACS comorbidity, for the subject is the probability of risk for that individual subject.

In particular embodiments, the methods further comprise: d) performing at least one of the following actions (or diagnosing the subject as in need of one of the following): i) performing coronary catheterization on the subject based, or inserting a stent, on the estimated risk of ACS being high, ii) treating the subject with a cardiovascular disease (CVD) therapeutic based on the estimated risk of ACS being high, iii) prescribing the subject a CVD therapeutic based on the estimated risk of ACS being high, iv) performing at least one additional diagnostic test on the subject based on the estimated risk of ACS, or estimated risk of an ACS comorbidity, being moderate, v) admitting and/or directing the subject to be admitted to a hospital or other treatment facility based on the estimated risk of ACS, and/or an ACS comorbidity, being high, vi) testing a sample from the subject with one or more non-troponin I CVD risk assays based on the estimated risk of ACS, and/or an ACS comorbidity, being moderate, vii) discharging the subject from a treatment facility based on the estimated risk of ACS, and/or an ACS comorbidity, being low, viii) performing a stress test on the subject based on the estimated risk of ACS being moderate, and viii) determining probability of risk for the subject for major adverse clinical event (MACE) in 30 days post discharge.

In further embodiments, the methods further comprise: d) performing at least one of the following actions: i) communicating the estimated risk of ACS, and/or an ACS comorbidity, for the subject to a user, ii) displaying the estimated risk of ACS, and/or an ACS comorbidity, for the subject, iii) generating a report providing the estimated risk of ACS, and/or an ACS comorbidity, and iv) preparing and/or transmitting a report providing the estimated risk of ACS, and/or an ACS comorbidity.

In certain embodiments, the obtaining subject values comprises receiving the subject values from a testing lab, from the subject, from an analytical testing system, and/or from a hand-held or point of care testing device. In other embodiments, the processing system further comprises the analytical testing system and/or the hand-held or point of care testing device. In other embodiments, the processing system is middleware in a larger computer system. In additional embodiments, the obtaining subject values comprises electronically receiving the subject values. In further embodiments, the obtaining subject values comprises testing the initial sample, the first subsequent sample, and/or the second subsequent sample with a cTnI and/or cTnT detection assay. In other embodiments, the cTnI and/or cTnT detection assay comprises a single molecule detection assay or a bead-based immunoassay. In particular embodiments, the ACS is selected from the group consisting of ST elevation myocardial infarction (STEMI), non ST elevation myocardial infarction (NSTEMI), unstable angina, Type I myocardial infraction, Type II myocardial infraction, chest pain, and chest pain presenting within three hours (known as early presenters) or less for medical care (e.g., less than 3 hours, less than 2 hours, or less than 1 hour). In certain embodiments, the ACS comorbidity is selected from the group consisting of: heart failure, metastatic tumour, renal disease (e.g., renal insufficiency), and diabetes.

In certain embodiments, the methods comprise manually or automatically inputting the subject values into the processing system. In additional embodiments, the subject is a human (e.g., a man or a woman that is 25 . . . 35 . . . 45 . . . 55 . . . 65 . . . 75 . . . 85 . . . or 95 years old). In particular embodiments, the subject is a human with chest pain. In other embodiments, the subject gender and/or subject age comprises subject gender. In certain embodiments, the at least one of the following comprises subject age. In additional embodiments, the at least one of the following comprises both subject age and subject gender.

In some embodiments, the initial sample from the subject comprises a blood, serum, or plasma sample. In additional embodiments, the initial sample is taken from the subject at an Emergency Room or urgent care clinic. In further embodiments, the first and/or second subsequent samples comprise blood, serum, or plasma samples. In other embodiments, the first and/or second subsequent samples are taken within 1-9 hours of the initial sample (e.g., with in 1 . . . 3 . . . 5 . . . 7 . . . or 9 hours). In additional embodiments, the first and/or second subsequent cTnI and/or cTnT concentration comprises both the first and second subsequent cTnI and/or cTnT concentrations. In certain embodiments, the subject values further comprise further comprise a subject measurement selected from the group consisting of: ECG measurement, hematology analysis of the subjects blood, medical history, results of physical, and current medications.

In some embodiments, the processing system further comprises a graphical user interface, and the method further comprises inputting the subject values is via the graphical user interface. In other embodiments, the graphical user interface is part of a device selected from: a desktop computer, a notebook computer, a tablet computer, a smart phone, and a point of care analytical device. In particular embodiments, the processing system further comprises a sample analyzer. In some embodiments, at least part of the computer memory is located inside the sample analyzer. In certain embodiments, the system further comprises a Laboratory Interface System (LIM). In other embodiments, the at least part of the computer memory is part of the LIM. In some embodiments, the system further comprises a processing device selected from the group consisting of: a desktop computer, a notebook computer, a tablet computer, a smart phone, and a point of care analytical device. In particular embodiments, the at least part of the computer memory is located inside the processing device. In further embodiments, the processing system further comprises a display component configured to display the estimated risk of ACS, and/or an ACS comorbidity, for the subject. In other embodiments, the display component is selected from a computer monitor, a tablet computer screen, a smart phone screen, and a point of care analytical device screen.

In additional embodiments, the rate of change algorithm subtracts the cTnI and/or cTnT concentration from a first subject sample taken at a first time from the cTnI and/or cTnT concentration from a second subject sample taken at a second time to generate a cTnI and/or cTnT difference, and then divides the cTnI and/or cTnT difference by the time difference which is calculated by subtracting the first time from the second time. In certain embodiments, the time difference is measured in minutes or seconds. In some embodiments, the first subject sample is the initial sample or the first subsequent sample, and the second subject sample is the first or second subsequent sample.

In certain embodiments, the at least M number of decision trees comprises at least five decision trees (e.g., 5 . . . 10 . . . 35 . . . 100 . . . 250 . . . 500 . . . 800 . . . 1000 or more). In some embodiments, the at least M number of decision trees comprises at least. 800 decision trees. In further embodiments, the pre-determined splitting variables and/or the predetermined terminal node values are empirically derived from analysis of population data. In other embodiments, the analysis of population data comprises employing a boosted decision tree model. In some embodiments, the at least M decision trees, as a group, employ at least three of the splitting variables. In other embodiments, the at least M decision trees, as a group, at least four, or at least five, or at least six, of the splitting variables.

In additional embodiments, the threshold rate of change value is cTnI and/or cTnT concentration change per minute. In other embodiments, the subject age value is either the subject's age in years or an set value based on range of ages. In particular embodiments, the set value is determined based on the following ranges: 0-29 years old, 30-39 years old, 40-49 years old, 50-59 years old, 60-69 years old, 70-79 years old, and 80 years old or older. In some embodiments, the gender value is one number for males (e.g., 1.0) and a lower number for females (e.g., 0.1 or 0).

In certain embodiments, the combined value is either a non-weighted or a weighted combined value. In additional embodiments, the weighted value is summation of all of the terminal node values multiplied by a weight value. In further embodiments, the combined value from M number of terminal nodes is a weighted combined valued represented by the formula:

$$\sum_{i=1}^{M} a_i T_i(X, \beta_i),$$

where $T_i$ represents the individual decision trees, X represents the subject values, $\beta_i$ presents the at least two splitting variables, $a_i$ represents a weight value, and $$\sum_{i=1}^{M}$$

represents summing together all of the M decision trees. In further embodiments, the process the combined value to determine an estimated risk of ACS, and/or ACS comorbidity, for the subject comprises solving the following equation:

$$\log\frac{p1}{1-p1} = \sum_{i=1}^{M} a_i T_i(X, \beta_i),$$

where p1 represents the estimated risk of ACS or ACS comorbidity. In additional embodiments, the combined score is represented by the following formula:

$$\text{Sum Score: } SS = \left(\frac{1}{2}\right)\times\sum_{i=0}^{n=814}\text{score}_i + \left(\frac{1}{2}\right)\times\ln\frac{(1-0.727646454265159)}{(1+0.727646454265159)}.$$

This formula is shown with n=814, which is the number of trees. The number of trees may be a different number, such as the 987 shown in Appendix B, or a number from 3 to 10,000 (e.g., 3 . . . 100 . . . 1000 . . . 5000 . . . 10,000).

In certain embodiments, the non-transitory computer memory further comprises an subject index look up table (e.g., as shown in Table 1), and wherein the process the combined value to determine an estimated risk of ACS, and/or an ACS comorbidity, for the subject comprises: i) applying the combined value to the following formula to find a Sum Score (SS):

$$\text{Sum Score: } SS = \left(\frac{1}{2}\right)\times\sum_{i=1}^{M}\text{score}_i + \left(\frac{1}{2}\right)\times\ln\frac{(1-0.727646454265159)}{(1+0.727646454265159)},$$

ii) applying the SS to the following formula to find the Final Index (IDX):

$$\text{Final Index: } IDX = \frac{1}{\left(1 + \exp^{(-2 \times SS)}\right)} \times 100,$$

and iii) applying the IDX to the subject index look up table to determine the estimated risk of ACS, and/or an ACS comorbidity, for the subject.

BRIEF DESCRIPTION OF THE FIGURES

FIG. 4 shows a hypothetical exemplary patient report. This report indicates that the results of testing this patient's parameters (e.g., initial troponin concentration, troponin rate, age, and gender) with the algorithms described herein could generate an Index value of 2.59, a Sensitivity of 98.8% and NPV (negative predictive value) of 99.73%. In light of these values, this patient has a low risk of ACS. Therefore, this patient could be recommended (e.g., by the treating physician or clinic or hospital staff) to not undergo further CVD testing, and could be recommended that CVD therapeutics were not necessary.

DEFINITIONS

Figure 1A:
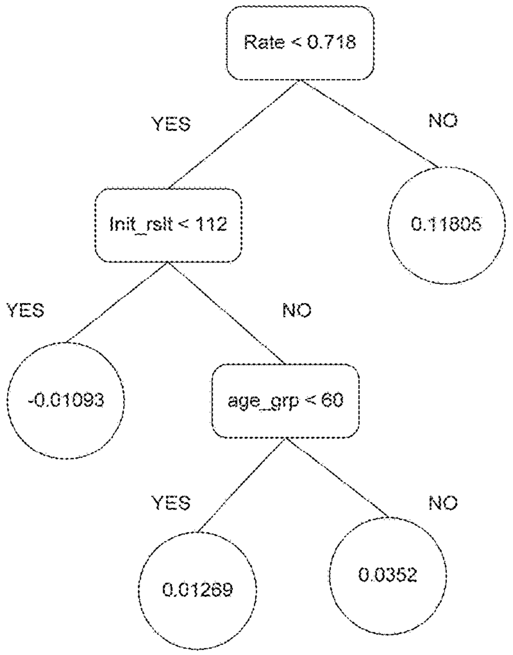
FIG. 1A shows an example of a decision tree. This exemplary decision tree shows three splitting variables (for cTnI rate, initial cTnI result, and age; all shown by rectangles), and four terminal nodes based on where a particular patient falls within the splitting variables (shown by circles).

The term "acute coronary syndrome" as used herein refers to a group of conditions due to decreased blood flow in the coronary arteries such that part of the heart muscle is unable to function properly or dies. The most common symptom is chest pain, often radiating to the left arm or angle of the jaw, pressure-like in character, and associated with nausea and sweating. Acute coronary syndrome usually occurs as a result of one of three problems: ST elevation myocardial infarction (STEMI, 30%), non ST elevation myocardial infarction (NSTEMI, 25%), or unstable angina (38%) (Torres and Moayedi, 2007 Clin. Geriatr. Med. 23 (2): 307-25, vi; herein incorporated by reference in its entirety). These types are named according to the appearance of the electrocardiogram (ECG/EKG) as non-ST segment elevation myocardial infarction and ST segment elevation myocardial infarction. There can be some variation as to which forms of myocardial infarction (MI) are classified under acute coronary syndrome. ACS should be distinguished from stable angina, which develops during exertion and resolves at rest. In contrast with stable angina, unstable angina occurs suddenly, often at rest or with minimal exertion, or at lesser degrees of exertion than the individual's previous angina ("crescendo angina"). New onset angina is also considered unstable angina, since it suggests a new problem in a coronary artery. Though ACS is usually associated with coronary thrombosis, it can also be associated with cocaine use. Cardiac chest pain can also be precipitated by anemia, bradycardias (excessively slow heart rate) or tachycardias (excessively fast heart rate). The cardinal symptom of decreased blood flow to the heart is chest pain, experienced as tightness around the chest and radiating to the left arm and the left angle of the jaw. This may be associated with diaphoresis (sweating), nausea and vomiting, as well as shortness of breath. In many cases, the sensation is "atypical," with pain experienced in different ways or even being completely absent (which is more likely in female patients and those with diabetes). Some may report palpitations, anxiety or a sense of impending doom (angor animi) and a feeling of being acutely ill. Patients with chest-pain are entering the emergency rooms of hospitals very frequently. Chest-pain, however, can result from many causes: gastric discomfort (e.g. indigestion), pulmonary distress, pulmonary embolism, dyspnea, musculoskeletal pain (pulled muscles, bruises) indigestion, pneumothorax, cardiac non-coronary conditions, and acute ischemic coronary syndrome (ACS). As mentioned above, ACS is usually one of three diseases involving the coronary arteries: ST elevation myocardial infarction (30%), non ST elevation myocardial infarction (25%), or unstable angina (38%). These types are named according to the appearance of the electrocardiogram (ECG/EKG) as non-ST segment elevation myocardial infarction (NSTEMI) and ST segment elevation myocardial infarction (STEMI). ACS is usually associated with coronary thrombosis. The physician has to decide if the patient is having a life threatening ischemic ACS or not. In the case of such an ischemic cardiac event, rapid treatment by opening up the occluded coronary artery is essential to prevent further loss of myocardial tissue.

As used herein, "suspected of having acute coronary syndrome" means a subject has at least one of the symptoms of acute coronary syndrome described above (e.g., chest pain or experiencing tightness around the chest and radiating to the left arm and the left angle of the jaw).

As used herein, the term "diagnosis" "diagnosis" can encompass determining the nature of disease in a subject, as well as determining the severity and probable outcome of disease or episode of disease and/or prospect of recovery (prognosis). "Diagnosis" can also encompass diagnosis in the context of rational therapy, in which the diagnosis guides therapy, including initial selection of therapy, modification of therapy (e.g., adjustment of dose and/or dosage regimen or lifestyle change recommendations), and the like.

The terms "individual," "host," "subject," and "patient" are used interchangeably herein, and generally refer to a pregnant mammal, including, but not limited to, primates, including simians and humans, equines (e.g., horses), canines (e.g., dogs), felines, various domesticated livestock (e.g., ungulates, such as swine, pigs, goats, sheep, and the like), as well as domesticated pets and animals maintained in zoos. In some embodiments, the subject is specifically a human subject.

Before the present invention is further described, it is to be understood that this invention is not limited to particular embodiments described, as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a sample" includes a plurality of such samples and reference to a specific protein includes reference to one or more specific proteins and equivalents thereof known to those skilled in the art, and so forth.

DETAILED DESCRIPTION OF THE INVENTION

The invention provides decision tree based systems and methods for estimating the risk of acute coronary syndrome (ACS), and/or an ACS comorbidity, in subjects suspect of having ACS and/or an ACS comorbidity. In particular, systems and methods are provided that employ additive decision tree based algorithms to process a subject's initial cardiac troponin I or T (cTnI or cTnT) concentration, a subject's cTnI and/or cTnT rate of change, and the subject's age and/or gender to generate an estimate risk of ACS, and/or an ACS comorbidity. Such risk stratification allows, for example, patients to be ruled in or rule out with regard to needing urgent treatment.

In certain embodiments, provided herein are processing systems and methods that allow an input of a first and a second troponin result, age and gender variables. These variable inputs are evaluated via a decision tree based statistical calculation to provide an estimated risk of ACS, and/or an ACS comorbidity, such that that a subject can be stratified into appropriate categories of risk. In particular embodiments, the systems and methods herein address the variable of timing between sample collection by determining the rate of change of troponin based on the exact time or nearly exact time (e.g., in minutes) of the first collection and the second collection of the sample from the subject. The systems and methods herein, in certain embodiments, address the age variable by determining the impact of the age decile the patient falls into. The systems and methods herein, in some embodiments, addresses the gender difference by categorizing the patients into male and female gender profiles.

The systems and methods herein considers the patient variables and determines the appropriate risk category of the patient. For example, in work conducted during the development of embodiments of the present invention, the systems and methods herein categorized approximately 87 percent of the suspected ACS patients into low risk category allowing for safe rule out of these patients from having myocardial infraction (MI); and also categorized appropriately 8% of the suspect ACS population into high risk category for having an MI, which addresses the patients that need to be triaged to the cardiac catheterization lab. This helps address the overwhelming majority of presenting patients in the acute setting leaving, for example, only 4-6% of patients requiring additional workup or observation in the acute setting. Such risk stratification of suspected ACS patients (e.g., in the acute setting) helps to reduce false positives and false negatives, which reduces adverse outcomes as well as healthcare costs.

I. Decision Tree Algorithm

In certain embodiments, the estimated risk of ACS (e.g., MI) or an ACS comorbidity, is determined using an additive tree model. One example of such a model is a boosted decision tree model (also additive logistic model) which is a tree-based additive regression model. Mathematically, it can be expressed as, in the context of hs Troponin I or T diagnosis:

$$\log\frac{p_1}{1-p_1} = F(X) = \sum_{i=1}^{M} a_i T_i(X, \beta_i)$$

where p1=Prob (acute coronary syndrome, such as MI) and Ti(X,βi) is a decision tree of the X=(TnI or TnT Change Rate, Gender, Age, Initial TnI or Initial TnT result), characterized by parameters βi. The parameters βi are the splitting variables, split locations, and the terminal node predictions of the tree Ti. FIG. 1A is an example of Ti, in which the variable Age is not involved due to its relatively insignificant effect.

In FIG. 1A, the rectangles are the splitting variables and the corresponding split location values, and in the circles are the terminal node predictions of the tree Ti. For example, for a subject with TnI change rate=0.6, initial TnI result=500, age=40, and gender is male, the prediction value by the tree above is 0.01269 (the bottom left circle). The parameters M and ai are regularization parameters to balance the prediction error and the over-fitting of the model. In fact, the Boosted Decision Trees can be viewed as a weighted summation of multiple different decision trees. In certain embodiments, these trees are not grown independently, but rather sequentially. For example, if M=200 and ai=0.01, the right-hand side of (1), F(X), can be illustrated by the diagram in FIG. 1B.

Figure 1B:
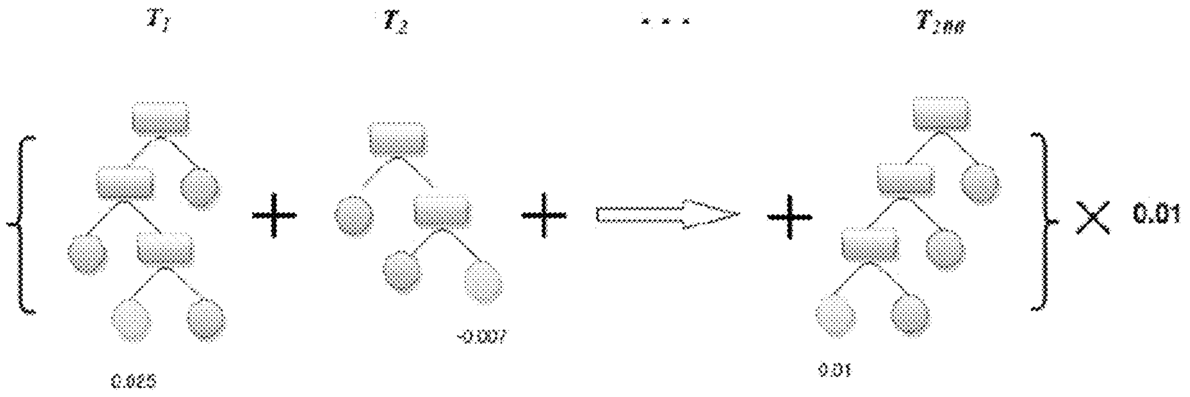
FIG. 1B shows a series of decision trees (from 1 to 200), and all of the terminal node values are added together and then multiplied by a weighting value (0.1).

It can be seen in FIG. 1B that this particular boosted decision trees model is a weighted summation of 200 different individual decision trees with the weight 0.01. The arrow in FIG. 1B implies that these individual trees are grown sequentially, that is, the later trees are grown depending on the former trees. Note that all the parameters in the model are to be determined by algorithms and rules.

For a specific subject with the information regarding the TnI change rate, initial TnI result, age, and gender, the prediction values from each tree can be obtained (e.g., from the circles having numbers by them). Then F(X) is actually obtained by (0.025-0.007+ . . . +0.01)×0.01. Assume this number is 0.2, thus from (1), p1=0.12. Note that p1 is a probability value between 0 and 1. The index of the subject is 12 obtained by multiplying p1 by 100.

II. Biological Samples

Biological samples from a subject are tested to determine the concentration of cardiac troponin I and or troponin T. Biological samples include, but are not necessarily limited to, bodily fluids such as blood-related samples (e.g., whole blood, serum, plasma, and other blood-derived samples), urine, cerebral spinal fluid, bronchoalveolar lavage, and the like. Another example of a biological sample is a tissue sample. A biological sample may be fresh or stored (e.g. blood or blood fraction stored in a blood bank). The biological sample may be a bodily fluid expressly obtained for the assays of this invention or a bodily fluid obtained for another purpose which can be sub-sampled for the assays of this invention. In certain embodiments, the biological sample is whole blood. Whole blood may be obtained from the subject using standard clinical procedures. In other embodiments, the biological sample is plasma. Plasma may be obtained from whole blood samples by centrifugation of anti-coagulated blood. Such process provides a buffy coat of white cell components and a supernatant of the plasma. In certain embodiments, the biological sample is serum. Serum may be obtained by centrifugation of whole blood samples that have been collected in tubes that are free of anti-coagulant. The blood is permitted to clot prior to centrifugation. The yellowish-reddish fluid that is obtained by centrifugation is the serum. In another embodiment, the sample is urine. The sample may be pretreated as necessary by dilution in an appropriate buffer solution, heparinized, concentrated if desired, or fractionated by any number of methods including but not limited to ultracentrifugation, fractionation by fast performance liquid chromatography (FPLC), or precipitation of apolipoprotein B containing proteins with dextran sulfate or other methods. Any of a number of standard aqueous buffer solutions at physiological pH, such as phosphate, Tris, or the like, can be used.

III. Exemplary Detection Assays

The present invention is not limited by the type of assay used to detect cardiac troponin I (cTnI) or troponin T (cTnT). In certain embodiments, the methods for detecting troponin I are as described in U.S. Patent Application Publication 2012/0076803 and U.S. Pat. No. 8,535,895, both of which are herein incorporated by reference, particularly for assay design. In particular embodiments, the methods for detecting troponin T employ the Elecsys® Troponin T high sensitive (TnT-hs) assay (ROCHE) (see, Li et al., Arch Cardiovasc Dis. 2016 March; 109(3):163-70, herein incorporated by reference in its entirety and particularly for a description of high sensitivity troponin T detection).

In certain embodiments, an immunoassay is employed for detecting cTnI and or cTnT. Any suitable assay known in the art can be used, including commercially available cTnI or cTnT assays. Examples of such assays include, but are not limited to, immunoassay, such as sandwich immunoassay (e.g., monoclonal-polyclonal sandwich immunoassays, including radioisotope detection (radioimmunoassay (RIA)) and enzyme detection (enzyme immunoassay (EIA) or enzyme-linked immunosorbent assay (ELISA) (e.g., Quantikine ELISA assays, R&D Systems, Minneapolis, Minn.)), competitive inhibition immunoassay (e.g., forward and reverse), fluorescence polarization immunoassay (FPIA), enzyme multiplied immunoassay technique (EMIT), bioluminescence resonance energy transfer (BRET), and homogeneous chemiluminescent assay, etc. In certain embodiments, cTnI is detected with the ERENNA detection assay system from Singulex Inc. or Abbott's hs TnI STAT ARCHITECT assay.

EXAMPLES

The following examples are for purposes of illustration only and are not intended to limit the scope of the claims.

Example 1

Testing a Patient Population

This example describes the testing of a population of 972 subjects, where 86 had myocardial infarction (MI) and 886 were non-MI patients. This testing allowed the development of the 815 tree database (M=815) that is shown in Appendix A, as well as the Index Reference table shown in Table 1 below.

TABLE 1

INDEX REFERENCE TABLE

| Index | Risk Level | Sensitivity (%) [95% CI] | Specificity (%) [95% CI] | PPV (%) [95% CI] | NPV (%) [95% CI] |
|---|---|---|---|---|---|
| 0.00 | Low risk | 100.00 [98.62, 100.00] | 0.00 [0.00, 0.22] | 13.62 [12.12, 15.22] | NA |
| 1.00 | Low risk | 100.00 [98.62, 100.00] | 13.80 [12.19, 15.54] | 15.46 [13.78, 17.26] | 100.00 [98.42, 100.00] |
| 2.00 | Low risk | 98.87 [96.73, 99.77] | 60.56 [58.18, 62.91] | 28.32 [25.44, 31.35] | 99.71 [99.14, 99.94] |
| 3.00 | Low risk | 98.11 [95.65, 99.38] | 70.61 [68.37, 72.78] | 34.48 [31.09, 38.00] | 99.58 [99.02, 99.86] |
| 4.00 | Mod. risk | 96.23 [93.17, 98.18] | 78.35 [76.30, 80.29] | 41.20 [37.29, 45.19] | 99.25 [98.62, 99.64] |
| 5.00 | Mod. risk | 95.09 [91.76, 97.36] | 82.51 [80.61, 84.30] | 46.15 [41.91, 50.44] | 99.07 [98.42, 99.50] |
| 6.00 | Mod. risk | 94.34 [90.84, 96.80] | 85.37 [83.58, 87.02] | 50.40 [45.91, 54.89] | 98.97 [98.30, 99.42] |
| 7.00 | Mod. risk | 92.83 [89.03, 95.63] | 87.98 [86.33, 89.50] | 54.91 [50.17, 59.58] | 98.73 [98.03, 99.23] |
| 8.00 | Mod. risk | 90.94 [86.82, 94.11] | 89.77 [88.22, 91.18] | 58.35 [53.43, 63.15] | 98.43 [97.68, 98.99] |
| 9.00 | Mod. risk | 89.81 [85.52, 93.18] | 90.96 [89.48, 92.29] | 61.03 [55.99, 65.89] | 98.26 [97.49, 98.85] |
| 10.00 | Mod. risk | 89.43 [85.09, 92.86] | 91.49 [90.06, 92.78] | 62.37 [57.28, 67.26] | 98.21 [97.43, 98.81] |
| 11.00 | Mod. risk | 89.06 [84.66, 92.55] | 92.09 [90.69, 93.33] | 63.96 [58.83, 68.86] | 98.16 [97.37, 98.77] |
| 12.00 | Mod. risk | 88.68 [84.23, 92.23] | 92.56 [91.20, 93.77] | 65.28 [60.11, 70.19] | 98.11 [97.31, 98.72] |
| 13.00 | Mod. risk | 88.30 [83.81, 91.91] | 92.92 [91.59, 94.10] | 66.29 [61.09, 71.21] | 98.05 [97.25, 98.67] |
| 14.00 | Mod. risk | 88.30 [83.81, 91.91] | 93.40 [92.10, 94.54] | 67.83 [62.61, 72.73] | 98.06 [97.26, 98.68] |
| 15.00 | Mod. risk | 87.55 [82.96, 91.27] | 93.58 [92.30, 94.70] | 68.24 [63.00, 73.15] | 97.95 [97.13, 98.58] |
| 16.00 | Mod. risk | 87.55 [82.96, 91.27] | 93.81 [92.55, 94.92] | 69.05 [63.80, 73.95] | 97.95 [97.13, 98.58] |
| 17.00 | Mod. risk | 87.55 [82.96, 91.27] | 93.93 [92.68, 95.03] | 69.46 [64.21, 74.36] | 97.95 [97.14, 98.59] |
| 18.00 | Mod. risk | 87.55 [82.96, 91.27] | 94.23 [93.01, 95.30] | 70.52 [65.27, 75.39] | 97.96 [97.15, 98.59] |
| 19.00 | Mod. risk | 86.79 [82.11, 90.63] | 94.23 [93.01, 95.30] | 70.34 [65.06, 75.24] | 97.84 [97.01, 98.49] |
| 20.00 | Mod. risk | 86.79 [82.11, 90.63] | 94.29 [93.07, 95.35] | 70.55 [65.28, 75.45] | 97.84 [97.01, 98.49] |
| 21.00 | Mod. risk | 86.79 [82.11, 90.63] | 94.29 [93.07, 95.35] | 70.55 [65.28, 75.45] | 97.84 [97.01, 98.49] |
| 22.00 | Mod. risk | 86.79 [82.11, 90.63] | 94.53 [93.33, 95.57] | 71.43 [66.16, 76.30] | 97.84 [97.02, 98.49] |
| 23.00 | Mod. risk | 86.42 [81.69, 90.30] | 94.71 [93.52, 95.73] | 72.01 [66.73, 76.88] | 97.79 [96.95, 98.45] |
| 24.00 | Mod. risk | 85.66 [80.85, 89.65] | 95.00 [93.85, 95.99] | 72.99 [67.69, 77.85] | 97.68 [96.82, 98.35] |
| 25.00 | Mod. risk | 84.91 [80.02, 88.99] | 95.00 [93.85, 95.99] | 72.82 [67.49, 77.70] | 97.56 [96.69, 98.25] |
| 26.00 | Mod. risk | 84.53 [79.60, 88.66] | 95.24 [94.11, 96.21] | 73.68 [68.35, 78.55] | 97.50 [96.63, 98.20] |
| 27.00 | Mod. risk | 83.77 [78.77, 88.00] | 95.48 [94.37, 96.42] | 74.50 [69.15, 79.35] | 97.39 [96.50, 98.11] |
| 28.00 | Mod. risk | 83.02 [77.95, 87.34] | 95.54 [94.44, 96.47] | 74.58 [69.21, 79.45] | 97.27 [96.37, 98.01] |
| 29.00 | Mod. risk | 81.51 [76.30, 86.00] | 95.72 [94.64, 96.63] | 75.00 [69.58, 79.89] | 97.04 [96.11, 97.81] |
| 30.00 | Mod. risk | 81.13 [75.89, 85.66] | 95.90 [94.83, 96.79] | 75.70 [70.29, 80.58] | 96.99 [96.05, 97.76] |
| 31.00 | Mod. risk | 81.13 [75.89, 85.66] | 96.19 [95.16, 97.06] | 77.06 [71.67, 81.86] | 97.00 [96.06, 97.77] |
| 32.00 | Mod. risk | 80.38 [75.08, 84.98] | 96.25 [95.23, 97.11] | 77.17 [71.76, 81.99] | 96.89 [95.94, 97.67] |
| 33.00 | Mod. risk | 80.00 [74.67, 84.64] | 96.37 [95.36, 97.21] | 77.66 [72.24, 82.46] | 96.83 [95.88, 97.62] |
| 34.00 | Mod. risk | 80.00 [74.67, 84.64] | 96.61 [95.63, 97.42] | 78.81 [73.44, 83.54] | 96.84 [95.89, 97.62] |
| 35.00 | Mod. risk | 79.25 [73.86, 83.97] | 96.73 [95.76, 97.53] | 79.25 [73.86, 83.97] | 96.73 [95.76, 97.53] |
| 36.00 | Mod. risk | 79.25 [73.86, 83.97] | 96.73 [95.76, 97.53] | 79.25 [73.86, 83.97] | 96.73 [95.76, 97.53] |
| 37.00 | Mod. risk | 78.87 [73.45, 83.62] | 97.09 [96.16, 97.84] | 81.01 [75.68, 85.61] | 96.68 [95.71, 97.48] |
| 38.00 | Mod. risk | 78.11 [72.65, 82.94] | 97.14 [96.23, 97.89] | 81.18 [75.83, 85.78] | 96.57 [95.59, 97.39] |
| 39.00 | Mod. risk | 77.74 [72.24, 82.60] | 97.26 [96.37, 97.99] | 81.75 [76.41, 86.31] | 96.52 [95.53, 97.34] |
| 40.00 | Mod. risk | 77.74 [72.24, 82.60] | 97.38 [96.50, 98.09] | 82.40 [77.10, 86.91] | 96.52 [95.54, 97.34] |
| 41.00 | Mod. risk | 77.74 [72.24, 82.60] | 97.50 [96.64, 98.19] | 83.06 [77.81, 87.51] | 96.53 [95.54, 97.34] |
| 42.00 | Mod. risk | 76.98 [71.44, 81.91] | 97.62 [96.77, 98.29] | 83.61 [78.35, 88.02] | 96.42 [95.42, 97.25] |
| 43.00 | Mod. risk | 76.60 [71.04, 81.57] | 97.68 [96.84, 98.35] | 83.88 [78.63, 88.28] | 96.36 [95.36, 97.20] |
| 44.00 | Mod. risk | 75.85 [70.23, 80.88] | 97.74 [96.91, 98.40] | 84.10 [78.84, 88.50] | 96.25 [95.24, 97.10] |
| 45.00 | Mod. risk | 75.47 [69.83, 80.53] | 97.74 [96.91, 98.40] | 84.03 [78.75, 88.45] | 96.19 [95.17, 97.05] |
| 46.00 | Mod. risk | 75.47 [69.83, 80.53] | 97.80 [96.98, 98.45] | 84.39 [79.13, 88.76] | 96.20 [95.18, 97.05] |
| 47.00 | Mod. risk | 75.09 [69.43, 80.18] | 97.80 [96.98, 98.45] | 84.32 [79.04, 88.71] | 96.14 [95.12, 97.00] |
| 48.00 | Mod. risk | 74.34 [68.64, 79.49] | 97.86 [97.05, 98.50] | 84.55 [79.26, 88.94] | 96.03 [94.99, 96.90] |
| 49.00 | High risk | 73.21 [67.45, 78.44] | 97.86 [97.05, 98.50] | 84.35 [79.00, 88.79] | 95.86 [94.81, 96.75] |
| 50.00 | High risk | 73.21 [67.45, 78.44] | 97.98 [97.18, 98.60] | 85.09 [79.79, 89.45] | 95.87 [94.82, 96.76] |
| 51.00 | High risk | 73.21 [67.45, 78.44] | 97.98 [97.18, 98.60] | 85.09 [79.79, 89.45] | 95.87 [94.82, 96.76] |
| 52.00 | High risk | 72.83 [67.05, 78.09] | 98.10 [97.32, 98.69] | 85.78 [80.52, 90.06] | 95.82 [94.76, 96.71] |
| 53.00 | High risk | 72.83 [67.05, 78.09] | 98.10 [97.32, 98.69] | 85.78 [80.52, 90.06] | 95.82 [94.76, 96.71] |
| 54.00 | High risk | 72.08 [66.26, 77.39] | 98.10 [97.32, 98.69] | 85.65 [80.35, 89.97] | 95.71 [94.64, 96.61] |
| 55.00 | High risk | 71.32 [65.47, 76.69] | 98.10 [97.32, 98.69] | 85.52 [80.18, 89.88] | 95.59 [94.52, 96.51] |
| 56.00 | High risk | 70.57 [64.68, 75.98] | 98.16 [97.39, 98.74] | 85.78 [80.43, 90.13] | 95.49 [94.40, 96.42] |
| 57.00 | High risk | 70.19 [64.29, 75.63] | 98.16 [97.39, 98.74] | 85.71 [80.34, 90.08] | 95.43 [94.34, 96.37] |
| 58.00 | High risk | 70.19 [64.29, 75.63] | 98.22 [97.46, 98.79] | 86.11 [80.77, 90.43] | 95.43 [94.34, 96.37] |
| 59.00 | High risk | 70.19 [64.29, 75.63] | 98.27 [97.53, 98.84] | 86.51 [81.21, 90.78] | 95.44 [94.34, 96.37] |
| 60.00 | High risk | 69.43 [63.50, 74.92] | 98.27 [97.53, 98.84] | 86.38 [81.04, 90.69] | 95.33 [94.22, 96.27] |
| 61.00 | High risk | 69.06 [63.11, 74.57] | 98.39 [97.67, 98.94] | 87.14 [81.85, 91.35] | 95.28 [94.17, 96.23] |
| 62.00 | High risk | 68.68 [62.72, 74.21] | 98.39 [97.67, 98.94] | 87.08 [81.76, 91.31] | 95.22 [94.11, 96.18] |
| 63.00 | High risk | 68.30 [62.33, 73.86] | 98.39 [97.67, 98.94] | 87.02 [81.68, 91.27] | 95.17 [94.05, 96.13] |
| 64.00 | High risk | 68.30 [62.33, 73.86] | 98.39 [97.67, 98.94] | 87.02 [81.68, 91.27] | 95.17 [94.05, 96.13] |
| 65.00 | High risk | 67.17 [61.16, 72.79] | 98.45 [97.74, 98.99] | 87.25 [81.89, 91.50] | 95.01 [93.88, 95.98] |
| 66.00 | High risk | 66.04 [59.99, 71.72] | 98.57 [97.88, 99.08] | 87.94 [82.59, 92.12] | 94.85 [93.71, 95.84] |
| 67.00 | High risk | 65.28 [59.22, 71.00] | 98.69 [98.03, 99.18] | 88.72 [83.42, 92.79] | 94.75 [93.59, 95.74] |
| 68.00 | High risk | 65.28 [59.22, 71.00] | 98.93 [98.31, 99.36] | 90.58 [85.52, 94.32] | 94.76 [93.61, 95.75] |
| 69.00 | High risk | 64.53 [58.44, 70.29] | 98.99 [98.39, 99.41] | 90.96 [85.92, 94.64] | 94.65 [93.50, 95.66] |
| 70.00 | High risk | 64.53 [58.44, 70.29] | 98.99 [98.39, 99.41] | 90.96 [85.92, 94.64] | 94.65 [93.50, 95.66] |
| 71.00 | High risk | 64.53 [58.44, 70.29] | 99.11 [98.53, 99.50] | 91.94 [87.05, 95.42] | 94.66 [93.50, 95.66] |
| 72.00 | High risk | 63.77 [57.67, 69.57] | 99.23 [98.68, 99.59] | 92.86 [88.10, 96.14] | 94.56 [93.39, 95.57] |
| 73.00 | High risk | 62.26 [56.13, 68.12] | 99.41 [98.91, 99.71] | 94.29 [89.74, 97.23] | 94.35 [93.17, 95.38] |
| 74.00 | High risk | 61.89 [55.74, 67.76] | 99.41 [98.91, 99.71] | 94.25 [89.68, 97.21] | 94.30 [93.12, 95.33] |

TABLE 1-continued

INDEX REFERENCE TABLE

| Index | Risk Level | Sensitivity (%) [95% CI] | Specificity (%) [95% CI] | PPV (%) [95% CI] | NPV (%) [95% CI] |
|---|---|---|---|---|---|
| 75.00 | High risk | 61.13 [54.98, 67.04] | 99.41 [98.91, 99.71] | 94.19 [89.57, 97.18] | 94.19 [93.00, 95.24] |
| 76.00 | High risk | 60.75 [54.59, 66.67] | 99.41 [98.91, 99.71] | 94.15 [89.51, 97.16] | 94.14 [92.95, 95.19] |
| 77.00 | High risk | 58.49 [52.30, 64.49] | 99.41 [98.91, 99.71] | 93.94 [89.14, 97.06] | 93.82 [92.60, 94.90] |
| 78.00 | High risk | 56.23 [50.02, 62.29] | 99.46 [98.99, 99.75] | 94.30 [89.46, 97.36] | 93.51 [92.27, 94.61] |
| 79.00 | High risk | 54.72 [48.51, 60.82] | 99.46 [98.99, 99.75] | 94.16 [89.20, 97.29] | 93.30 [92.05, 94.42] |
| 80.00 | High risk | 53.21 [47.00, 59.34] | 99.46 [98.99, 99.75] | 94.00 [88.92, 97.22] | 93.10 [91.82, 94.22] |
| 81.00 | High risk | 51.70 [45.50, 57.85] | 99.46 [98.99, 99.75] | 93.84 [88.62, 97.14] | 92.89 [91.60, 94.03] |
| 82.00 | High risk | 51.32 [45.13, 57.48] | 99.46 [98.99, 99.75] | 93.79 [88.54, 97.12] | 92.84 [91.55, 93.99] |
| 83.00 | High risk | 50.94 [44.75, 57.11] | 99.46 [98.99, 99.75] | 93.75 [88.47, 97.10] | 92.79 [91.49, 93.94] |
| 84.00 | High risk | 49.43 [43.26, 55.62] | 99.64 [99.22, 99.87] | 95.62 [90.71, 98.38] | 92.59 [91.29, 93.76] |
| 85.00 | High risk | 46.79 [40.66, 53.00] | 99.70 [99.31, 99.90] | 96.12 [91.19, 98.73] | 92.24 [90.91, 93.43] |
| 86.00 | High risk | 43.40 [37.34, 49.60] | 99.70 [99.31, 99.90] | 95.83 [90.54, 98.63] | 91.79 [90.43, 93.00] |
| 87.00 | High risk | 40.38 [34.42, 46.55] | 99.76 [99.39, 99.94] | 96.40 [91.03, 99.01] | 91.39 [90.01, 92.63] |
| 88.00 | High risk | 38.49 [32.60, 44.64] | 99.76 [99.39, 99.94] | 96.23 [90.62, 98.96] | 91.14 [89.75, 92.40] |
| 89.00 | High risk | 36.60 [30.79, 42.72] | 99.82 [99.48, 99.96] | 97.00 [91.48, 99.38] | 90.90 [89.49, 92.17] |
| 90.00 | High risk | 35.47 [29.71, 41.56] | 99.82 [99.48, 99.96] | 96.91 [91.23, 99.36] | 90.75 [89.34, 92.03] |
| 91.00 | High risk | 33.21 [27.56, 39.23] | 99.94 [99.67, 100.00] | 98.88 [93.90, 99.97] | 90.47 [89.04, 91.77] |
| 92.00 | High risk | 27.92 [22.61, 33.74] | 99.94 [99.67, 100.00] | 98.67 [92.79, 99.97] | 89.79 [88.33, 91.13] |
| 93.00 | High risk | 25.66 [20.51, 31.36] | 100.00 [99.78, 100.00] | 100.00 [94.72, 100.00] | 89.51 [88.04, 90.86] |
| 94.00 | High risk | 19.25 [14.68, 24.52] | 100.00 [99.78, 100.00] | 100.00 [93.02, 100.00] | 88.71 [87.20, 90.10] |
| 95.00 | High risk | 12.45 [8.73, 17.04] | 100.00 [99.78, 100.00] | 100.00 [89.42, 100.00] | 87.87 [86.33, 89.30] |
| 96.00 | High risk | 5.66 [3.20, 9.16] | 100.00 [99.78, 100.00] | 100.00 [78.20, 100.00] | 87.05 [85.47, 88.52] |
| 97.00 | High risk | 1.89 [0.62, 4.35] | 100.00 [99.78, 100.00] | 100.00 [47.82, 100.00] | 86.60 [85.01, 88.09] |
| 98.00 | High risk | 0.00 [0.00, 1.38] | 100.00 [99.78, 100.00] | NA | 86.38 [84.78, 87.88] |
| 99.00 | High risk | 0.00 [0.00, 1.38] | 100.00 [99.78, 100.00] | NA | 86.38 [84.78, 87.88] |
| 100.00 | High risk | 0.00 [0.00, 1.38] | 100.00 [99.78, 100.00] | NA | 86.38 [84.78, 87.88] |

Example 2

Determining ACS Risk in a Patient

This example describes an exemplary method for determining ACS risk in a patient. A patient presents to an emergency room with chest pain. The relevant patient information is collected from the patient by questioning the patient and testing an initial and second blood sample from the patient to determine cardiac troponin I concentration. The patient information is presented in Table 2 below.

TABLE 2

| Initial TnI Rslt | Initial TnI Rslt Time | Second Result | Second Result Time | Rate | Gender | Age | Age deciles |
|---|---|---|---|---|---|---|---|
| 15.3 | 14:50 | 13.8 | 15:50 | −0.025 | 0 (Female) | 86 | 7 |

The TnI Rate (per minute) is calculated by using the difference between the two hs TnI concentration values divided by the corresponding difference between collection time (in minutes) from the first two available time points of the subject. Next, age is categorized into deciles (1-7) as follows: '<30' (1), '30-<40' (2), '40-<50' (3), '50-<60' (3), '60-<70' (4), '70-<80' (6), '80 or older' (7). This patient was 86, so they were a "7" in age deciles. The gender is assigned based on the following: Female=0, Male=1. Therefore, this patient, as a female, was assigned the value of zero for gender.

Figure 2:
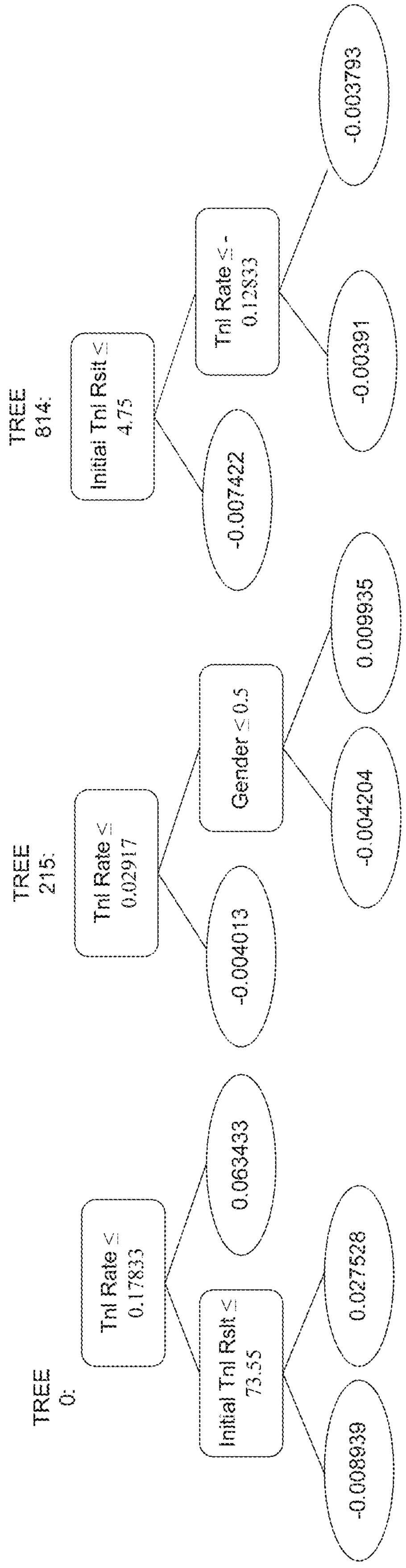
FIG. 2 shows 3 of the 815 decisions trees from Example 2 in graphic form that correspond to 3 of the 815 trees shown in database form in Appendix A.
Figure 3:
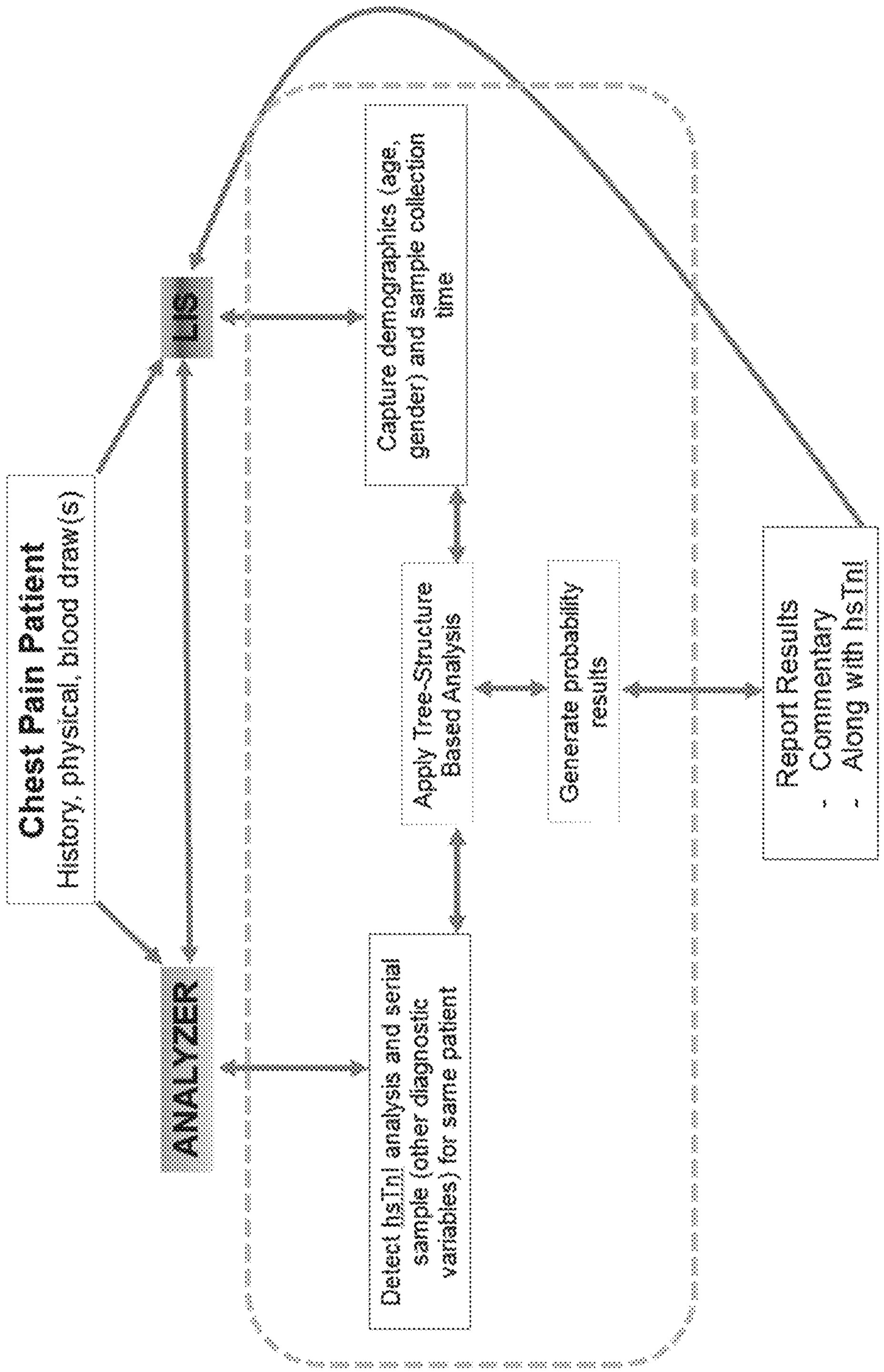
FIG. 3 shows an exemplary flow diagram of how information may be entered and processed in the systems and methods described herein. For example, blood may be drawn from a subject with chest pain a number of times to determine initial cTnI concentration and subsequent cTnI concentration using the analyzer shown in the figure. The information from the analyzer, as well as the patients age and gender, is then entered into a laboratory information system (LIS). Such information is then provided to the tree-structure based analysis system to generate an estimated risk of acute coronary syndrome. This risk, along with appropriate commentary, may be provided as a report and fed back into the LIS, such that it can be available to the treating doctor and/or the patient.

Next, the values from table 2 for this patient are applied a pre-determined series of decision trees. In this example, the values for this patient are applied to the database of 815 decisions trees in Appendix A (trees 0 to 814). FIG. 2 shows three of the 815 trees from Appendix A in diagrammatic form, which includes Tree 0, Tree 215, and Tree 814. Tree 0 shows, for example, cTnI rate ≤0.17833 as a splitting variable. One would split down to the left if less than or equal to 0.17833, and splits down to the right if not less than or equal to 0.17833. The patient in this example had a rate of 0.025, so one splits down to the left. Spitting down to the left, one encounters the spitting variable box of Initial cTnI result of ≤73.55. This patient has an initial concentration of 15.3 pg/ml, therefore, one splits down to the left and encounters terminal node −0.008939, which is therefore the value of this tree.

Appendix A has the same decision trees, but in database form. The first column in Appendix A contains the tree number (0-814). The second column contains the node label (0-6). The third column contains the split variables (0=TnI rate (in mins), 1=initial TnI rslt, 2=gender, 3=age_grp, −1=terminal node). The fourth column contains the cutoff value for each split variable. If less than or equal to the cutoff value, then go to the 'leftnode,' if greater than the cutoff value then go to the 'rightnode.' The 'leftnode' and 'rightnode' columns contain the number of the next node that one is to go to.

The database works as follows to form decision trees as follows. Table 3 shows the first seven rows of Appendix A. These seven rows are labeled tree 0, and collectively form one of the 815 decision trees in Appendix A. Using the patient information from Table 2 above, the decision tree works as follows. One starts with the first row, which presents the splitting variable of TnI rate ≤0.178333333. If the patient meets this, then employ the 'leftnode' column which says go to node "1." If the patient does not meet this splitting variable, then employ the "rightnode" column, which says to go to node "5." Since this patient is less than 0.17833333, then the leftnode column is used, which says to go to node 1. Node 1 is found in the next row. The splitting variable for this next row is 'initial TnI rslt' with a value of less than or equal to 73.55. Since this patient has an initial TnI value ≤73.55, then go to 'leftnode,' which this time 'leftnode' says go to '2'. So again look at the 'node' column look for '2' which happens to be the next row again. This time the split variable is 'terminal node,' meaning the end node of the tree has been reached, so read the value in 'prediction' column of this row, which is −0.008939. Therefore, −0.008939 is the outcome score for tree 0 for this patient, and is highlighted in Appendix A. Repeat the same logic through the rest 814 trees. This patient will have total 815 outcome scores from these 815 trees. These outcomes are all highlighted in Appendix A.

TABLE 3

| Tree | Node | Splitvar | Split cutoff | LeftNode | RightNode | Prediction | Splitvar1 |
|---|---|---|---|---|---|---|---|
| 0 | 0 | 0 | 0.178333333 | 1 | 5 | −0.00074264 | Rate |
| 0 | 1 | 1 | 73.55 | 2 | 3 | −0.006885553 | Initial_rslt |
| 0 | 2 | −1 | −0.008938888 | 7 | 7 | −0.008938888 | terminal |
| 0 | 3 | −1 | 0.027528344 | 7 | 7 | 0.027528344 | terminal |
| 0 | 4 | −1 | −0.006885553 | 7 | 7 | −0.006885553 | terminal |
| 0 | 5 | −1 | 0.063432738 | 7 | 7 | 0.063432738 | terminal |
| 0 | 6 | −1 | −0.00074264 | 7 | 7 | −0.00074264 | terminal |

Next, the values from each of the trees is used in an additive tree formulas, such as, for example, the following. The following two formulas can be used to find an index score for this patient:

$$\text{Sum Score: } SS = \left(\frac{1}{2}\right)\times\sum_{i=0}^{n=814}\text{score}_i + \left(\frac{1}{2}\right)\times\ln\frac{(1-0.727646454265159)}{(1+0.727646454265159)}$$

$$\text{Final Index: } IDX = \frac{1}{\left(1+\exp^{(-2\times SS)}\right)}\times 100$$

The numbers for this particular patient can be plugged into the formula as follows:

$$SS = \frac{1}{2}\times(-0.008939+\cdots+(-0.004013)+\cdots+(-0.003793)) + \left(\frac{1}{2}\right)\times\ln\frac{(1-0.727646454265159)}{(1+0.727646454265159)} = -1.60788$$

$$\text{Final Index: } IDX = \frac{1}{\left(1+\exp^{(-2\times(-1.60788))}\right)}\times 100 = 3.86$$

The final index (3.86) is then compared to index reference table (Table 1 above, or Table 4 below) for probability statistics

TABLE 4

| Index | Sensitivity (%) [95% CI] | Specificity (%) [95% CI] | PPV (%) [95% CI] | NPV (%) [95% CI] |
|---|---|---|---|---|
| 3.85 | 96.60 [93.65, 98.44] | 77.22 [75.13, 79.20] | 40.06 [36.24, 43.98] | 99.31 [98.70, 99.68] |
| 3.86 | 96.60 [93.65, 98.44] | 77.33 [75.26, 79.32] | 40.19 [36.36, 44.11] | 99.31 [98.70, 99.69] |
| 3.87 | 96.60 [93.65, 98.44] | 77.33 [75.26, 79.32] | 40.19 [36.36, 44.11] | 99.31 [98.70, 99.69] |

Looking at table 1, with an index value of 3.86, this patient would be considered to have a moderate risk of ACS.

Example 3

Determining ACS Risk in a Patient

This example describes an exemplary method for determining ACS risk in a patient. A patient presents to an emergency room with chest pain. The relevant patient information is collected from the patient by questioning the patient and testing an initial and second blood sample from the patient to determine cardiac troponin I concentration. The patient information is presented in Table 5 below.

TABLE 5

| Initial TnI Rslt | Initial TnI Rslt Time | Second Result | Second Result Time | Rate | Gender | Age deciles |
|---|---|---|---|---|---|---|
| 15.3 | 14:50 | 13.8 | 15:50 | −0.025 | 0 (Female) | 7 (86) |

The TnI Rate (per minute) is calculated by using the difference between the two hs TnI concentration values divided by the corresponding difference between collection time (in minutes) from the first two available time points of the subject. Next, age is categorized into deciles (1-7) as follows: '<30' (1), '30-<40' (2), '40-<50' (3), '50-<60' (3), '60-<70' (4), '70-<80' (6), '80 or older' (7). This patient was 86, so they were a "7" in age deciles. The gender is assigned based on the following: Female=0, Male=1. Therefore, this patient, as a female, was assigned the value of zero for gender.

Figure 5:
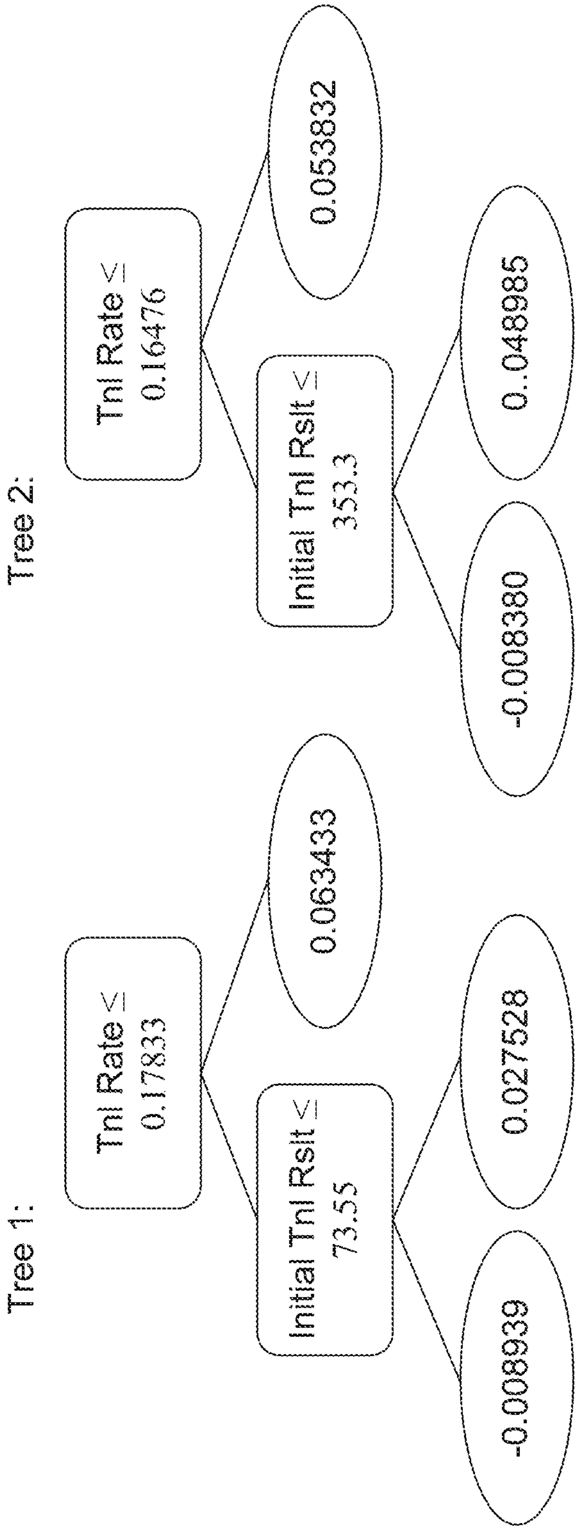
FIG. 5 shows the two decision trees from Example 3.

Next, the values from table 5 for this patient are applied a pre-determined series of two decision trees, which are shown in FIG. 5. Given this patients values, this patient will have total of 2 outcome scores (−0.008939 and −0.008380) from these 2 trees in FIG. 5.

Next, the values from each of the trees is used in an additive tree formulas, such as, for example, the following. The following two formulas can be used to find an index score for this patient:

$$\text{Sum Score: } SS = \left(\frac{1}{2}\right)\times\sum_{i=1}^{n=814}\text{score}_i + \left(\frac{1}{2}\right)\times\ln\frac{(1-0.727646454265159)}{(1+0.727646454265159)}$$

$$\text{Final Index: } IDX = \frac{1}{\left(1+\exp^{(-2\times SS)}\right)}\times 100$$

The numbers for this particular patient can be plugged into the formula as follows:

$$SS = \frac{1}{2}\times(-0.008939+(-0.008380)) + \frac{1}{2}\times\ln\frac{(1-0.727646454265159)}{(1+0.727646454265159)} = -0.932366$$

$$\text{Final Index: } IDX = \frac{1}{\left(1+\exp^{(-2\times(-0.932366))}\right)}\times 100 = 13.42$$

The final index (13.42) is then compared to index reference table (Table 1 above, or Table 6 below) for probability statistics.

TABLE 6

| Index | Sensitivity (%) [95% CI] | Specificity (%) [95% CI] | PPV (%) [95% CI] | NPV (%) [95% CI] |
|---|---|---|---|---|
| 13.41 | 88.30 [83.81, 91.91] | 93.16 [91.85, 94.32] | 67.05 [61.84, 71.96] | 98.06 [97.26, 98.68] |
| 13.42 | 88.30 [83.81, 91.91] | 93.16 [91.85, 94.32] | 67.05 [61.84, 71.96] | 98.06 [97.26, 98.68] |
| 13.43 | 88.30 [83.81, 91.91] | 93.16 [91.85, 94.32] | 67.05 [61.84, 71.96] | 98.06 [97.26, 98.68] |

Looking at Table 1, with an index value of 13.42 (using two trees as above), this patient would be considered to have a moderate risk of ACS.

When more trees are added to the algorithm, the index score converges to the index value of 3.86 from 815-tree algorithm described in Example 2 above. For example, a 10-tree algorithm gives an index value of 12.67, while a 50-tree algorithm gives an index value of 9.60.

Example 4

Risk Stratification of Patients of Suspected Myocardial Infarction

This example describes an exemplary method for employing algorithms to risk stratify patients of having myocardial infarction. As high-sensitivity cardiac troponin I concentrations vary by age, sex and time, it was desired to employ a risk estimating decision tool that incorporated these variables to improve the risk stratification and diagnosis of patients with suspected myocardial infarction (MI). Machine learning was used in a derivation cohort of 3,013 patients with suspected myocardial infarction to apply the risk estimating algorithm to predict type 1 MI. The algorithm incorporates age, sex, and paired high-sensitivity cardiac troponin I concentrations.

The MI3 Index value for each patient produced can be used for risk stratification. Validation was performed in a cohort of 7,998 patients by calibration curves, areas under the receiver operator characteristic curves (AUC), and performance at pre-specified thresholds. Optimal index thresholds for allocation to low-risk (Negative Predictive Value ≥99.5% and sensitivity ≥99.0%) and high-risk groups (Positive Predictive Value ≥75% and specificity ≥90%) were derived.

MI occurred in 404 (13.4%) and 849 (10.6%) patients in the derivation and validation cohorts respectively. Diagnostic performance of the risk estimating Index in the validation cohort was similar to the derivation cohort with good calibration and similar AUCs (0.963 [95% CI 0.956 to 0.971] cf 0.963 [0.957 to 0.968]). The optimal low-risk and high risk thresholds (1.1 and 57.1 respectively) categorized 51.6% of patients as low-risk and 10.3% as high-risk.

METHODS

Study Design

This exampled provides a retrospective analysis of prospectively collected data from multiple centers to derive and validate a risk estimating algorithm to facilitate decision making in patients presenting with suspected myocardial infarction. The risk estimating algorithm incorporates age, sex, paired high-sensitivity cardiac troponin I concentrations and rate of change of cardiac troponin concentrations. These variables were selected a priori because they (a) were not subjective, (b) can be automatically captured from electronic hospital records, (c) were based on serial cardiac troponin measurements as recommended by the international guidelines, and (d) are known to be associated with the diagnosis of type 1 myocardial infarction.

Risk Estimating Algorithm

The risk estimating algorithm was built with a derivation cohort by a machine learning technique called boosting and comprises multiple decision trees which weight the input variables to optimally discriminate between those with and without the event.[20] The algorithm calculates a risk estimating Index (on a scale from 0-100) which predicts the likelihood of a diagnosis of type 1 myocardial infarction during the index hospital visit.

The machine learning technique, Boosting (also called Additive Logistic Model)[20], was applied to the derivation cohort to determine the decision trees and weightings for the final model (algorithm). Input was the initial hs-cTnI concentration, hs-cTnI change rate (the difference between the two serial hs-cTnI values divided by the difference in time in minutes), sex, age (categorized as: <30 (category 1), 30-<40 (2), 40-<50 (3), 50-<60 (4), 60-<70 (5), 70-<80 (6), 80 or older (7)), and type 1 myocardial infarction status. Mathematically, the model can be expressed as:

$$\log\frac{p_1}{1-p_1} = F_M(X) = F_0(X) + \sum_{i=1}^{M} a_i T_i(X)$$

where $p_1$=Probability of a Type 1 MI and $T_i(X,\beta_i)$ is a decision tree of the X=(hs-cTnI change rate, Sex, Age category, Initial hs-cTnI) characterized by parameters $\beta_i$, and M is the number of decision trees. $a_i$ is the weighting for each decision tree. Boosting was chosen because it is resistant to overfitting.[20] Once the decision trees and weightings are determined, they are locked in place. This example used a total of 987 trees, which are shown in Appendix B. The optimal M was determined by 5-fold cross validation and $a_i$ was set as 0.01. The final algorithm returned an index value (between 0 and 100) for each patient that reflects the probability of Type 1 MI.

Within the derivation cohort, risk estimating Index thresholds to risk stratify patients as low- or high-risk of having myocardial infarction were identified. Table 9 below presents the index threshold table, where the threshold value is listed in whole numbers. It is noted that the table could be expanded 100 fold by listing the threshold values in 0.01 increments.

TABLE 9

INDEX REFERENCE TABLE

| Index Cutoff | Risk level | MI Pos | MI Neg | Non-MI Pos | Non-MI Neg | Sensitivity (%) [95% CI] | Specificity (%) [95% CI] | PPV (%) [95% CI] | NPV (%) [95% CI] |
|---|---|---|---|---|---|---|---|---|---|
| 0.00 | low | 404 | 0 | 2609 | 0 | 100.00 [99.09, 100.00] | 0.00 [0.00, 0.14] | 13.41 [12.21, 14.68] | 99.92 [99.53, 100.00]* |
| 1.00 | low | 403 | 1 | 142 | 1186 | 99.75 [98.63, 99.99] | 45.46 [43.53, 47.39] | 22.07 [20.19, 24.04] | 99.92 [99.53, 100.00] |
| 2.00 | Mod. | 400 | 4 | 741 | 1868 | 99.01 [97.48, 99.73] | 71.60 [69.83, 73.32] | 35.06 [32.29, 37.91] | 99.79 [99.45, 99.94] |
| 3.00 | Mod. | 395 | 9 | 564 | 2045 | 97.77 [95.81, 98.98] | 78.38 [76.75, 79.95] | 41.19 [38.05, 44.38] | 99.56 [99.17, 99.80] |
| 4.00 | Mod. | 391 | 13 | 465 | 2144 | 96.78 [94.56, 98.28] | 82.18 [80.65, 83.63] | 45.68 [42.30, 49.08] | 99.40 [98.97, 99.68] |
| 5.00 | Mod. | 387 | 17 | 440 | 2169 | 95.79 [93.35, 97.53] | 83.14 [81.64, 84.55] | 46.80 [43.35, 50.26] | 99.22 [98.76, 99.55] |
| 6.00 | Mod. | 385 | 19 | 420 | 2189 | 95.30 [92.75, 97.15] | 83.90 [82.43, 85.29] | 47.83 [44.33, 51.34] | 99.14 [98.66, 99.48] |

TABLE 9-continued

INDEX REFERENCE TABLE

| Index Cutoff | Risk level | MI Pos | MI Neg | Non-MI Pos | Non-MI Neg | Sensitivity (%) [95% CI] | Specificity (%) [95% CI] | PPV (%) [95% CI] | NPV (%) [95% CI] |
|---|---|---|---|---|---|---|---|---|---|
| 7.00 | Mod. | 382 | 22 | 409 | 2200 | 94.55 [91.87, 96.56] | 84.32 [82.87, 85.70] | 48.29 [44.76, 51.84] | 99.01 [98.50, 99.38] |
| 8.00 | Mod. | 379 | 25 | 388 | 2221 | 93.81 [91.00, 95.96] | 85.13 [83.70, 86.47] | 49.41 [45.82, 53.01] | 98.89 [98.36, 99.28] |
| 9.00 | Mod. | 379 | 25 | 378 | 2231 | 93.81 [91.00, 95.96] | 85.51 [84.10, 86.84] | 50.07 [46.44, 53.69] | 98.89 [98.37, 99.28] |
| 10.00 | Mod. | 378 | 26 | 350 | 2259 | 93.56 [90.71, 95.75] | 86.58 [85.22, 87.87] | 51.92 [48.22, 55.61] | 98.86 [98.34, 99.26] |
| 11.00 | Mod. | 375 | 29 | 327 | 2282 | 92.82 [89.85, 95.14] | 87.47 [86.13, 88.71] | 53.42 [49.65, 57.16] | 98.75 [98.20, 99.16] |
| 12.00 | Mod. | 372 | 32 | 308 | 2301 | 92.08 [89.00, 94.52] | 88.19 [86.89, 89.41] | 54.71 [50.88, 58.49] | 98.63 [98.07, 99.06] |
| 13.00 | Mod. | 370 | 34 | 299 | 2310 | 91.58 [88.44, 94.10] | 88.54 [87.25, 89.74] | 55.31 [51.45, 59.12] | 98.55 [97.98, 98.99] |
| 14.00 | Mod. | 368 | 36 | 284 | 2325 | 91.09 [87.88, 93.68] | 89.11 [87.86, 90.28] | 56.44 [52.54, 60.29] | 98.48 [97.90, 98.93] |
| 15.00 | Mod. | 367 | 37 | 275 | 2334 | 90.84 [87.60, 93.47] | 89.46 [88.22, 90.61] | 57.17 [53.23, 61.03] | 98.44 [97.86, 98.90] |
| 16.00 | Mod. | 366 | 38 | 266 | 2343 | 90.59 [87.32, 93.26] | 89.80 [88.58, 90.94] | 57.91 [53.95, 61.79] | 98.40 [97.82, 98.87] |
| 17.00 | Mod. | 362 | 42 | 261 | 2348 | 89.60 [86.21, 92.40] | 90.00 [88.78, 91.12] | 58.11 [54.12, 62.01] | 98.24 [97.63, 98.73] |
| 18.00 | Mod. | 361 | 43 | 254 | 2355 | 89.36 [85.93, 92.19] | 90.26 [89.06, 91.38] | 58.70 [54.69, 62.62] | 98.21 [97.59, 98.70] |
| 19.00 | Mod. | 360 | 44 | 252 | 2357 | 89.11 [85.66, 91.97] | 90.34 [89.14, 91.45] | 58.82 [54.81, 62.75] | 98.17 [97.55, 98.67] |
| 20.00 | Mod. | 358 | 46 | 241 | 2368 | 88.61 [85.11, 91.54] | 90.76 [89.59, 91.85] | 59.77 [55.72, 63.72] | 98.09 [97.47, 98.60] |
| 21.00 | Mod. | 357 | 47 | 235 | 2374 | 88.37 [84.83, 91.33] | 90.99 [89.83, 92.06] | 60.30 [56.23, 64.27] | 98.06 [97.43, 98.57] |
| 22.00 | Mod. | 353 | 51 | 220 | 2389 | 87.38 [83.74, 90.45] | 91.57 [90.43, 92.61] | 61.61 [57.48, 65.61] | 97.91 [97.26, 98.44] |
| 23.00 | Mod. | 350 | 54 | 207 | 2402 | 86.63 [82.92, 89.80] | 92.07 [90.96, 93.07] | 62.84 [58.67, 66.86] | 97.80 [97.14, 98.34] |
| 24.00 | Mod. | 347 | 57 | 199 | 2410 | 85.89 [82.11, 89.14] | 92.37 [91.29, 93.36] | 63.55 [59.36, 67.60] | 97.69 [97.02, 98.25] |
| 25.00 | Mod. | 343 | 61 | 191 | 2418 | 84.90 [81.03, 88.25] | 92.68 [91.61, 93.65] | 64.23 [60.00, 68.30] | 97.54 [96.85, 98.11] |
| 26.00 | Mod. | 338 | 66 | 182 | 2427 | 83.66 [79.69, 87.13] | 93.02 [91.98, 93.97] | 65.00 [60.73, 69.10] | 97.35 [96.64, 97.95] |
| 27.00 | Mod. | 337 | 67 | 175 | 2434 | 83.42 [79.42, 86.91] | 93.29 [92.26, 94.22] | 65.82 [61.53, 69.92] | 97.32 [96.61, 97.92] |
| 28.00 | Mod. | 334 | 70 | 172 | 2437 | 82.67 [78.62, 86.24] | 93.41 [92.39, 94.33] | 66.01 [61.70, 70.13] | 97.21 [96.49, 97.82] |
| 29.00 | Mod. | 334 | 70 | 168 | 2441 | 82.67 [78.62, 86.24] | 93.56 [92.55, 94.47] | 66.53 [62.22, 70.65] | 97.21 [96.49, 97.82] |
| 30.00 | Mod. | 333 | 71 | 162 | 2447 | 82.43 [78.36, 86.01] | 93.79 [92.80, 94.69] | 67.27 [62.94, 71.39] | 97.18 [96.46, 97.79] |
| 31.00 | Mod. | 330 | 74 | 156 | 2453 | 81.68 [77.56, 85.33] | 94.02 [93.04, 94.90] | 67.90 [63.55, 72.03] | 97.07 [96.34, 97.69] |
| 32.00 | Mod. | 330 | 74 | 151 | 2458 | 81.68 [77.56, 85.33] | 94.21 [93.25, 95.08] | 68.61 [64.25, 72.73] | 97.08 [96.34, 97.70] |
| 33.00 | Mod. | 328 | 76 | 149 | 2460 | 81.19 [77.03, 84.88] | 94.29 [93.33, 95.15] | 68.76 [64.39, 72.90] | 97.00 [96.26, 97.63] |
| 34.00 | Mod. | 328 | 76 | 144 | 2465 | 81.19 [77.03, 84.88] | 94.48 [93.53, 95.33] | 69.49 [65.12, 73.62] | 97.01 [96.27, 97.64] |
| 35.00 | Mod. | 328 | 76 | 140 | 2469 | 81.19 [77.03, 84.88] | 94.63 [93.70, 95.47] | 70.09 [65.71, 74.20] | 97.01 [96.28, 97.64] |
| 36.00 | Mod. | 326 | 78 | 137 | 2472 | 80.69 [76.50, 84.43] | 94.75 [93.82, 95.57] | 70.41 [66.02, 74.53] | 96.94 [96.20, 97.57] |
| 37.00 | Mod. | 324 | 80 | 128 | 2481 | 80.20 [75.97, 83.97] | 95.09 [94.19, 95.89] | 71.68 [67.28, 75.79] | 96.88 [96.13, 97.52] |
| 38.00 | Mod. | 324 | 80 | 126 | 2483 | 80.20 [75.97, 83.97] | 95.17 [94.28, 95.96] | 72.00 [67.60, 76.10] | 96.88 [96.13, 97.52] |
| 39.00 | Mod. | 319 | 85 | 124 | 2485 | 78.96 [74.66, 82.83] | 95.25 [94.36, 96.03] | 72.01 [67.58, 76.14] | 96.69 [95.93, 97.35] |
| 40.00 | Mod. | 316 | 88 | 123 | 2486 | 78.22 [73.87, 82.15] | 95.29 [94.40, 96.07] | 71.98 [67.53, 76.14] | 96.58 [95.80, 97.25] |
| 41.00 | Mod. | 316 | 88 | 121 | 2488 | 78.22 [73.87, 82.15] | 95.36 [94.48, 96.14] | 72.31 [67.86, 76.46] | 96.58 [95.81, 97.25] |
| 42.00 | Mod. | 313 | 91 | 119 | 2490 | 77.48 [73.08, 81.46] | 95.44 [94.57, 96.21] | 72.45 [67.98, 76.62] | 96.47 [95.69, 97.15] |
| 43.00 | Mod. | 308 | 96 | 116 | 2493 | 76.24 [71.78, 80.31] | 95.55 [94.69, 96.31] | 72.64 [68.13, 76.83] | 96.29 [95.49, 96.99] |
| 44.00 | Mod. | 307 | 97 | 110 | 2499 | 75.99 [71.52, 80.08] | 95.78 [94.94, 96.52] | 73.62 [69.11, 77.79] | 96.26 [95.46, 96.96] |
| 45.00 | Mod. | 302 | 102 | 106 | 2503 | 74.75 [70.22, 78.92] | 95.94 [95.11, 96.66] | 74.02 [69.48, 78.21] | 96.08 [95.27, 96.80] |
| 46.00 | Mod. | 298 | 106 | 104 | 2505 | 73.76 [69.18, 77.99] | 96.01 [95.19, 96.73] | 74.13 [69.56, 78.34] | 95.94 [95.11, 96.66] |
| 47.00 | Mod. | 295 | 109 | 102 | 2507 | 73.02 [68.41, 77.29] | 96.09 [95.27, 96.80] | 74.31 [69.71, 78.54] | 95.83 [95.00, 96.57] |
| 48.00 | Mod. | 292 | 112 | 101 | 2508 | 72.28 [67.64, 76.59] | 96.13 [95.32, 96.84] | 74.30 [69.68, 78.55] | 95.73 [94.88, 96.47] |
| 49.00 | Mod. | 288 | 116 | 100 | 2509 | 71.29 [66.61, 75.65] | 96.17 [95.36, 96.87] | 74.23 [69.57, 78.51] | 95.58 [94.72, 96.33] |
| 50.00 | Mod. | 286 | 118 | 97 | 2512 | 70.79 [66.09, 75.18] | 96.28 [95.48, 96.97] | 74.67 [70.01, 78.95] | 95.51 [94.65, 96.27] |
| 51.00 | Mod. | 285 | 119 | 95 | 2514 | 70.54 [65.84, 74.95] | 96.36 [95.57, 97.04] | 75.00 [70.33, 79.28] | 95.48 [94.62, 96.24] |
| 52.00 | Mod. | 284 | 120 | 94 | 2515 | 70.30 [65.58, 74.71] | 96.40 [95.61, 97.08] | 75.13 [70.46, 79.41] | 95.45 [94.58, 96.21] |
| 53.00 | Mod. | 283 | 121 | 90 | 2519 | 70.05 [65.32, 74.48] | 96.55 [95.78, 97.22] | 75.87 [71.20, 80.13] | 95.42 [94.55, 96.18] |
| 54.00 | Mod. | 280 | 124 | 87 | 2522 | 69.31 [64.56, 73.77] | 96.67 [95.90, 97.32] | 76.29 [71.60, 80.55] | 95.31 [94.44, 96.09] |
| 55.00 | Mod. | 278 | 126 | 85 | 2524 | 68.81 [64.04, 73.30] | 96.74 [95.99, 97.39] | 76.58 [71.88, 80.85] | 95.25 [94.36, 96.02] |
| 56.00 | Mod. | 273 | 131 | 84 | 2525 | 67.57 [62.77, 72.12] | 96.78 [96.03, 97.42] | 76.47 [71.72, 80.78] | 95.07 [94.17, 95.86] |
| 57.00 | Mod. | 271 | 133 | 83 | 2526 | 67.08 [62.26, 71.65] | 96.82 [96.07, 97.46] | 76.55 [71.79, 80.87] | 95.00 [94.10, 95.80] |
| 58.00 | high | 270 | 134 | 78 | 2531 | 66.83 [62.01, 71.41] | 97.01 [96.28, 97.63] | 77.59 [72.84, 81.86] | 94.97 [94.07, 95.77] |
| 59.00 | high | 268 | 136 | 74 | 2535 | 66.34 [61.50, 70.93] | 97.16 [96.45, 97.77] | 78.36 [73.62, 82.61] | 94.91 [94.01, 95.71] |
| 60.00 | high | 263 | 141 | 69 | 2540 | 65.10 [60.23, 69.75] | 97.36 [96.66, 97.94] | 79.22 [74.45, 83.45] | 94.74 [93.83, 95.56] |
| 61.00 | high | 262 | 142 | 66 | 2543 | 64.85 [59.98, 69.51] | 97.47 [96.79, 98.04] | 79.88 [75.13, 84.08] | 94.71 [93.80, 95.53] |
| 62.00 | high | 259 | 145 | 64 | 2545 | 64.11 [59.22, 68.79] | 97.55 [96.88, 98.11] | 80.19 [75.41, 84.39] | 94.61 [93.69, 95.43] |
| 63.00 | high | 254 | 150 | 62 | 2547 | 62.87 [57.96, 67.60] | 97.62 [96.96, 98.17] | 80.38 [75.57, 84.61] | 94.44 [93.51, 95.27] |
| 64.00 | high | 248 | 156 | 58 | 2551 | 61.39 [56.45, 66.16] | 97.78 [97.14, 98.31] | 81.05 [76.20, 85.28] | 94.24 [93.29, 95.09] |
| 65.00 | high | 243 | 161 | 56 | 2553 | 60.15 [55.19, 64.96] | 97.85 [97.22, 98.37] | 81.27 [76.38, 85.53] | 94.07 [93.11, 94.93] |
| 66.00 | high | 234 | 170 | 52 | 2557 | 57.92 [52.94, 62.79] | 98.01 [97.39, 98.51] | 81.82 [76.85, 86.11] | 93.77 [92.79, 94.64] |
| 67.00 | high | 228 | 176 | 47 | 2562 | 56.44 [51.44, 61.33] | 98.20 [97.61, 98.67] | 82.91 [77.93, 87.16] | 93.57 [92.59, 94.46] |
| 68.00 | high | 221 | 183 | 41 | 2568 | 54.70 [49.71, 59.63] | 98.43 [97.87, 98.87] | 84.35 [79.38, 88.53] | 93.35 [92.35, 94.25] |
| 69.00 | high | 216 | 188 | 40 | 2569 | 53.47 [48.47, 58.41] | 98.47 [97.92, 98.90] | 84.38 [79.34, 88.60] | 93.18 [92.18, 94.09] |
| 70.00 | high | 208 | 196 | 34 | 2575 | 51.49 [46.49, 56.46] | 98.70 [98.18, 99.10] | 85.95 [80.92, 90.07] | 92.93 [91.91, 93.85] |
| 71.00 | high | 203 | 201 | 30 | 2579 | 50.25 [45.26, 55.23] | 98.85 [98.36, 99.22] | 87.12 [82.13, 91.14] | 92.77 [91.74, 93.71] |
| 72.00 | high | 196 | 208 | 24 | 2585 | 48.51 [43.54, 53.51] | 99.08 [98.63, 99.41] | 89.09 [84.20, 92.88] | 92.55 [91.52, 93.50] |
| 73.00 | high | 181 | 223 | 21 | 2588 | 44.80 [39.88, 49.80] | 99.20 [98.77, 99.50] | 89.60 [84.55, 93.45] | 92.07 [91.01, 93.04] |
| 74.00 | high | 171 | 233 | 17 | 2592 | 42.33 [37.46, 47.31] | 99.35 [98.96, 99.62] | 90.96 [85.92, 94.64] | 91.75 [90.68, 92.74] |
| 75.00 | high | 159 | 245 | 17 | 2592 | 39.36 [34.56, 44.31] | 99.35 [98.96, 99.62] | 90.34 [84.99, 94.27] | 91.36 [90.27, 92.37] |
| 76.00 | high | 148 | 256 | 15 | 2594 | 36.63 [31.92, 41.54] | 99.43 [99.05, 99.68] | 90.80 [85.28, 94.76] | 91.02 [89.91, 92.04] |
| 77.00 | high | 142 | 262 | 13 | 2596 | 35.15 [30.49, 40.02] | 99.50 [99.15, 99.73] | 91.61 [86.08, 95.46] | 90.83 [89.72, 91.87] |
| 78.00 | high | 131 | 273 | 11 | 2598 | 32.43 [27.88, 37.23] | 99.58 [99.25, 99.79] | 92.25 [86.56, 96.07] | 90.49 [89.36, 91.54] |
| 79.00 | high | 122 | 282 | 11 | 2598 | 30.20 [25.76, 34.93] | 99.58 [99.25, 99.79] | 91.73 [85.68, 95.80] | 90.21 [89.06, 91.27] |
| 80.00 | high | 111 | 293 | 9 | 2600 | 27.48 [23.18, 32.11] | 99.66 [99.35, 99.84] | 92.50 [86.24, 96.51] | 89.87 [88.71, 90.95] |

TABLE 9-continued

INDEX REFERENCE TABLE

| Index Cutoff | Risk level | MI Pos | MI Neg | Non-MI Pos | Non-MI Neg | Sensitivity (%) [95% CI] | Specificity (%) [95% CI] | PPV (%) [95% CI] | NPV (%) [95% CI] |
|---|---|---|---|---|---|---|---|---|---|
| 81.00 | high | 103 | 301 | 8 | 2601 | 25.50 [21.31, 30.04] | 99.69 [99.40, 99.87] | 92.79 [86.29, 96.84] | 89.63 [88.46, 90.71] |
| 82.00 | high | 95 | 309 | 6 | 2603 | 23.51 [19.46, 27.96] | 99.77 [99.50, 99.92] | 94.06 [87.52, 97.79] | 89.39 [88.21, 90.48] |
| 83.00 | high | 77 | 327 | 5 | 2604 | 19.06 [15.34, 23.23] | 99.81 [99.55, 99.94] | 93.90 [86.34, 97.99] | 88.84 [87.65, 89.96] |
| 84.00 | high | 66 | 338 | 5 | 2604 | 16.34 [12.87, 20.31] | 99.81 [99.55, 99.94] | 92.96 [84.33, 97.67] | 88.51 [87.30, 89.64] |
| 85.00 | high | 52 | 352 | 3 | 2606 | 12.87 [9.76, 16.53] | 99.89 [99.66, 99.98] | 94.55 [84.88, 98.86] | 88.10 [86.88, 89.25] |
| 86.00 | high | 39 | 365 | 2 | 2607 | 9.65 [6.95, 12.96] | 99.92 [99.72, 99.99] | 95.12 [83.47, 99.40] | 87.72 [86.48, 88.88] |
| 87.00 | high | 26 | 378 | 0 | 2609 | 6.44 [4.25, 9.29] | 100.00 [99.86, 100.00] | 100.00 [86.77, 100.00] | 87.35 [86.10, 88.52] |
| 88.00 | high | 20 | 384 | 0 | 2609 | 4.95 [3.05, 7.54] | 100.00 [99.86, 100.00] | 100.00 [83.16, 100.00] | 87.17 [85.92, 88.35] |
| 89.00 | high | 12 | 392 | 0 | 2609 | 2.97 [1.54, 5.13] | 100.00 [99.86, 100.00] | 100.00 [73.54, 100.00] | 86.94 [85.68, 88.12] |
| 90.00 | high | 5 | 399 | 0 | 2609 | 1.24 [0.40, 2.86] | 100.00 [99.86, 100.00] | 100.00 [47.82, 100.00] | 86.74 [85.47, 87.93] |
| 91.00 | high | 1 | 403 | 0 | 2609 | 0.25 [0.01, 1.37] | 100.00 [99.86, 100.00] | 100.00 [2.50, 100.00] | 86.62 [85.35, 87.82] |
| 92.00 | high | 1 | 403 | 0 | 2609 | 0.25 [0.01, 1.37] | 100.00 [99.86, 100.00] | 100.00 [2.50, 100.00] | 86.62 [85.35, 87.82] |
| 93.00 | high | 0 | 404 | 0 | 2609 | 0.00 [0.00, 0.91] | 100.00 [99.86, 100.00] | 100.00 [2.50, 100.00]* | 86.59 [85.32, 87.79] |
| 94.00 | high | 0 | 404 | 0 | 2609 | 0.00 [0.00, 0.91] | 100.00 [99.86, 100.00] | 100.00 [2.50, 100.00]* | 86.59 [85.32, 87.79] |
| 95.00 | high | 0 | 404 | 0 | 2609 | 0.00 [0.00, 0.91] | 100.00 [99.86, 100.00] | 100.00 [2.50, 100.00]* | 86.59 [85.32, 87.79] |
| 96.00 | high | 0 | 404 | 0 | 2609 | 0.00 [0.00, 0.91] | 100.00 [99.86, 100.00] | 100.00 [2.50, 100.00]* | 86.59 [85.32, 87.79] |
| 97.00 | high | 0 | 404 | 0 | 2609 | 0.00 [0.00, 0.91] | 100.00 [99.86, 100.00] | 100.00 [2.50, 100.00]* | 86.59 [85.32, 87.79] |
| 98.00 | high | 0 | 404 | 0 | 2609 | 0.00 [0.00, 0.91] | 100.00 [99.86, 100.00] | 100.00 [2.50, 100.00]* | 86.59 [85.32, 87.79] |
| 99.00 | high | 0 | 404 | 0 | 2609 | 0.00 [0.00, 0.91] | 100.00 [99.86, 100.00] | 100.00 [2.50, 100.00]* | 86.59 [85.32, 87.79] |
| 100.00 | high | 0 | 404 | 0 | 2609 | 0.00 [0.00, 0.91] | 100.00 [99.86, 100.00] | 100.00 [2.50, 100.00]* | 86.59 [85.32, 87.79] |

The risk estimating algorithm was validated in a second cohort by calibration curves, area under the receiver operator characteristic curve and performance of the derived risk estimating index threshold. Re-calibration of thresholds using all both cohort for optimal risk stratification and to improve generalizability followed.

Participants and Cohorts

Patients presenting with symptoms suggestive of myocardial infarction in whom serial high-sensitivity cardiac troponin I measurements were obtained at presentation and later within the emergency department were included. ST-segment elevation myocardial infarction (STEMI) patients were excluded. Cohorts were identified for inclusion if: they were prospective, included serial high-sensitivity cardiac troponin I concentrations, the final diagnosis was adjudicated according to the Universal Definition of Myocardial Infarction[4,23] and ethical approval permitted sharing of patient level data. Diagnosis was made with evidence of a rise and/or fall of cardiac troponin concentration with at least one value above the 99th percentile of a healthy population with at least one of the following: ischemic symptoms, new or presumed new significant ST-T wave changes or new left bundle branch block, development of pathological Q waves, imaging evidence of new loss of viable myocardium or new regional wall motion abnormality, and/or identification of an intracoronary thrombus by angiography or autopsy.[4,23] The algorithm was derived in patients recruited in Scotland and Germany.[9,24] The validation cohort was pooled from seven cohorts recruited in Australia, Germany, New Zealand, Spain, Switzerland, and the United States.[25-29]

Sampling and Laboratory Analysis

Cardiac troponin concentrations were measured at each study site by the Abbott ARCHITECT high sensitivity troponin I assay (Abbott diagnostics, Chicago, Illinois). The manufacturer reported limit of detection (LoD) and 99th percentile upper reference limit (URL) of the high-sensitivity assay are 1.9 ng/L and 26.2 ng/L respectively. The sex-specific 99th percentiles URLs are 16 ng/L for women and 34 ng/L for men.

Outcome Definitions and Adjudication

The primary outcome was the adjudicated diagnosis, using the Universal Definition, of type 1 myocardial infarction during the index admission. Diagnosis was made with evidence of a rise and/or fall of cardiac troponin concentration with at least one value above the $99^{th}$ percentile of a healthy population with at least one of the following: ischemic symptoms, new or presumed new significant ST-T wave changes or new left bundle branch block, development of pathological Q waves, imaging evidence of new loss of viable myocardium or new regional wall motion abnormality, and/or identification of an intracoronary thrombus by angiography or autopsy.[4,23]

Statistical Analysis

Boosting was applied to the derivation cohort to determine the decision trees and weightings for the final risk estimating. Once these were determined, they were locked in place and programmed into an excel spreadsheet that was used to return the risk estimating index values in the derivation and validation cohorts.

It was pre-specified that we would derive and validate risk estimating index value thresholds from the derivation cohort that provided a sensitivity of ≥99.0%, negative predictive value (NPV) of ≥99.5%, a specificity of ≥90% and a positive predictive value (PPV) of ≥75% for the diagnosis of type 1 myocardial infarction. The sensitivity target was based on a survey of what was considered an acceptable risk by physicians in the Emergency Department[30], and the NPV target was the most common in the literature. Specificity and PPV targets were chosen by consensus of the project steering committee as clinically reasonably for high-risk stratification. The risk estimating index value thresholds corresponding to these four diagnostic metrics were determined from the derivation cohort with 95% confidence intervals determined by bootstrapping (1,000 samples).

Algorithm performance was assessed in the derivation and validation cohorts with calibration curves, and discrimination with the area under the receiver operator characteristic curve (AUC). Index thresholds were validated and derived at the pre-specified statistical metrics. Two index value thresholds were re-calibrated using both the derivation and validation cohort for optimal performance to risk stratify patients to low-risk (Negative Predictive Value ≥99.5% and sensitivity ≥99.0%) and high-risk (Positive Predictive Value ≥75% and specificity ≥90%). Validation, performed independently of algorithm derivation, used R (version 3.2.4: The R Foundation for Statistical Computing).[31]

Sensitivity, Subgroup and Post-Hoc Analyses

Additional pre-planned subgroup analyses were: comparison by sex, age (≤65,>65), comorbidities (History of Coronary Artery Disease, Diabetes Mellitus, Hypertension, Current smoking), time from onset of symptoms to first sample draw, time between serial cardiac troponin testing, and in those patients without new evidence of myocardial ischemia on the electrocardiogram. Performance of the algorithm was also evaluated for type 1 myocardial infarction within 30 days.

Results

The derivation cohort comprised 3,013 patients of whom 404 (13.4%) had a diagnosis of type 1 myocardial infarction. The cohort was predominantly male (63%) with a mean age of 62.4 (Table 7).

TABLE 7

Baseline characteristics of derivation and validation cohorts

| Variable | Derivation (n = 3,013) | Validation (n = 7,998) |
|---|---|---|
| Age, years | 62.4 ± 14.9 | 58.8 ± 15.1 |
| Sex, female (%) | 1113 (36.9) | 3,058 (38.2) |
| History of CAD (%) | 1143 (37.9) | 2,143 (26.8) |
| History of MI (%) | 630 (21.1) | 1,599 (20.0) |
| Diabetes mellitus (%) | 436 (14.6) | 1,494 (18.7) |
| Dyslipidaemia | 1232 (41.3) | 3,835 (47.9) |
| Hypertension | 1,705 (57.2) | 4,570 (57.1) |
| Current smoker | 648 (21.9) | 1,957 (24.7) |
| Family history of CAD | 986 (33.9) | 3,197 (40.6) |
| Symptom onset to blood draw >3 h | 1,948 (67.0) | 4,385 (61.5) |

Values are mean ± standard deviation;
CAD = coronary artery disease,
MI = myocardial infarction The validation cohort comprised 7,998 patients of whom 849 (10.6%) had a diagnosis of type 1 myocardial infarction. Validation cohort patients were younger, less likely to have previous CAD, but more likely to smoke, have diabetes mellitus, hyperlipidemia, or a family history of CAD than the derivation cohort. A greater proportion had blood drawn within 3 hours of symptom onset than in the derivation cohort (38.5% versus 33.0%, p<0.0001). The time between sample draws (median 2.2 [IQR 2.0-2.6] hrs) was longer than for the derivation cohort (1.2 [1.0-2.5] hrs), P<0.0001.

Correlation and Discrimination

Figure 6:
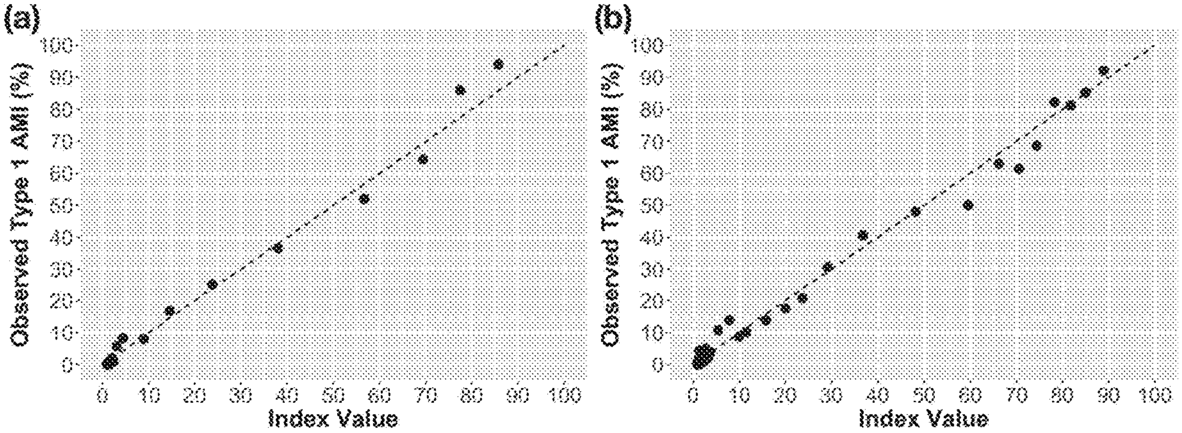
FIG. 6 shows a calibration of the risk estimating index with observed proportion of patients with type 1 myocardial infarction in the derivation (a) and validation cohorts (b). Each point represents the observed proportion of patients with type 1 myocardial infarction in a group of 100 patients for a given risk estimating index value. The dashed lines represent perfect calibration.
Figure 7:
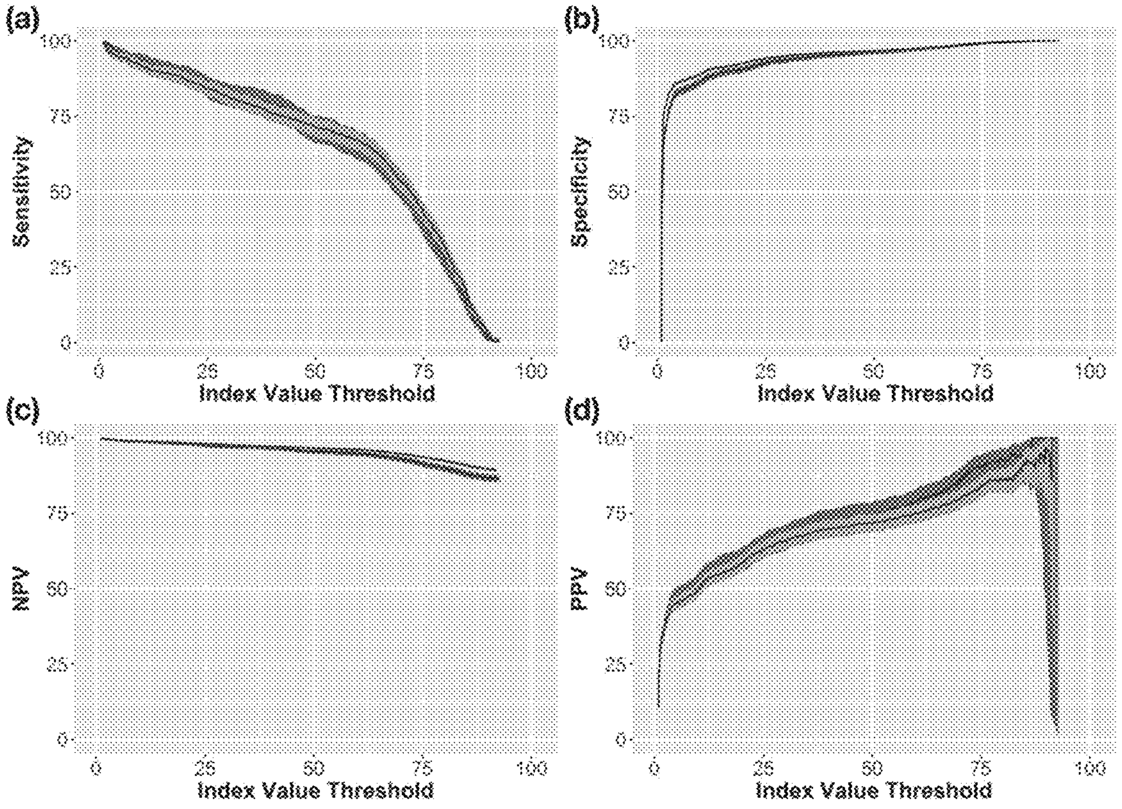
FIG. 7 shows performance of the risk estimating algorithm across its entire range (0 to 100) in the validation (grey) and derivation (gold) cohorts. Black lines are the point estimates at each index value thresholds and shaded regions 95% confidence intervals.

The risk estimating index value was well calibrated (FIG. 6) and the diagnostic metrics performed similarly across the entire risk estimating index range with only slightly lower PPV and NPV for the validation compared with the derivation cohorts (FIG. 7). The index discriminated between those with and without type 1 myocardial infarction in the derivation cohort (AUC 0.963 [95% CI 0.956 to 0.971]) and in the validation cohort (AUC 0.963 [95% CI 0.957 to 0.968]).

Performance of Diagnostic Thresholds

The risk estimating index thresholds from the derivation cohort that met the pre-specified diagnostic performance criteria were 1.6 (sensitivity ≥99.0%), 3.1 (NPV ≥99.5%), 17.2 (specificity ≥90.0%), and 49.7 (PPV ≥75%). (Table 8).

TABLE 8

MI3 risk estimating index thresholds from the derivation cohort

| Statistical thresholds | RISK ESTIMATING threshold (95% CI) | Proportion low risk, % | Proportion high risk, % |
|---|---|---|---|
| Sensitivity ≥99.0% | 1.6 (0.9 to 3.0) | 59.8% (57.9% to 61.5%) | — |
| NPV ≥99.5% | 3.1 (1.7 to 4.7) | 68.6% (66.9% to 70.2%) | — |
| Specificity of ≥90% | 17.2 (13.8 to 21.2) | — | 20.7% (19.2% to 22.1%) |
| PPV of ≥75% | 49.7 (36.6 to 60.0) | — | 12.8% (11.6% to 14.0%) |

NPV = negative predictive value,
PPV = positive predictive value

At the derived thresholds, the NPV (99.4% [99.2% to 99.6%]) and specificity (91.7% [91.1% to 92.3%]) were similar to the values used to derive the thresholds (99.5% for NPV, 90.0% for specificity). The sensitivity (97.8% [96.7% to 98.7%]) and PPV (71.8% [68.9% to 75.0%]) were slightly below the values (99.0% sensitivity and 75.0% PPV) used to derive the thresholds).

Recalibrated Optimal Diagnostic Thresholds

The optimal low-risk MI3 risk estimating index threshold was 1.1 (sensitivity 99.3% [98.8% to 99.7%]; NPV 99.8% [99.7% to 99.9%]) and optimal MI3 risk estimating index high-risk threshold was 57.1 (PPV 74.9% [72.5% to 77.4%]; Specificity 97.1% [96.7% to 97.4%]). Of the 11011 patients 5682 (51.6%) were classified as low-risk and 1134 (10.3) as high-risk.

Risk Estimating Thresholds Combined with ECG

Figure 8:
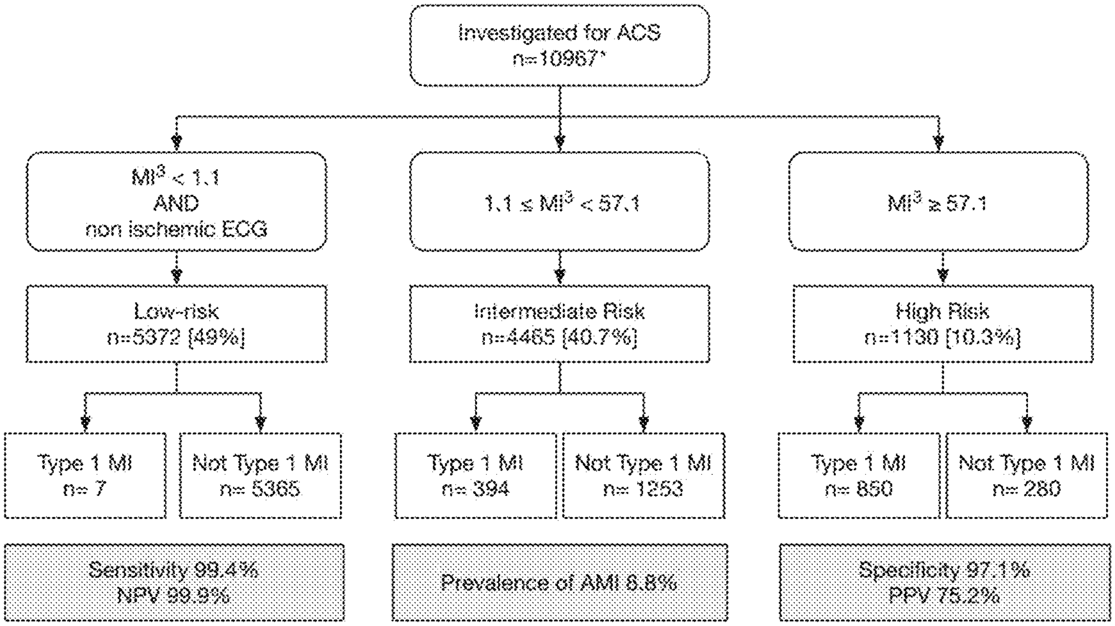
FIG. 8 shows a schema for clinical application incorporating ECG for low-risk stratification. *Note: only 10967 subjects had ECG classifications for this analysis.

The combination of a risk estimating index value <1.1 and no myocardial ischemia on the electrocardiogram had a sensitivity of 99.4% (99.0% to 99.8%) with a NPV of 99.9% (99.8 to 99.9%). 49.0% of patients were identified as low risk (FIG. 8).

Subgroup Analysis

Figure 9:
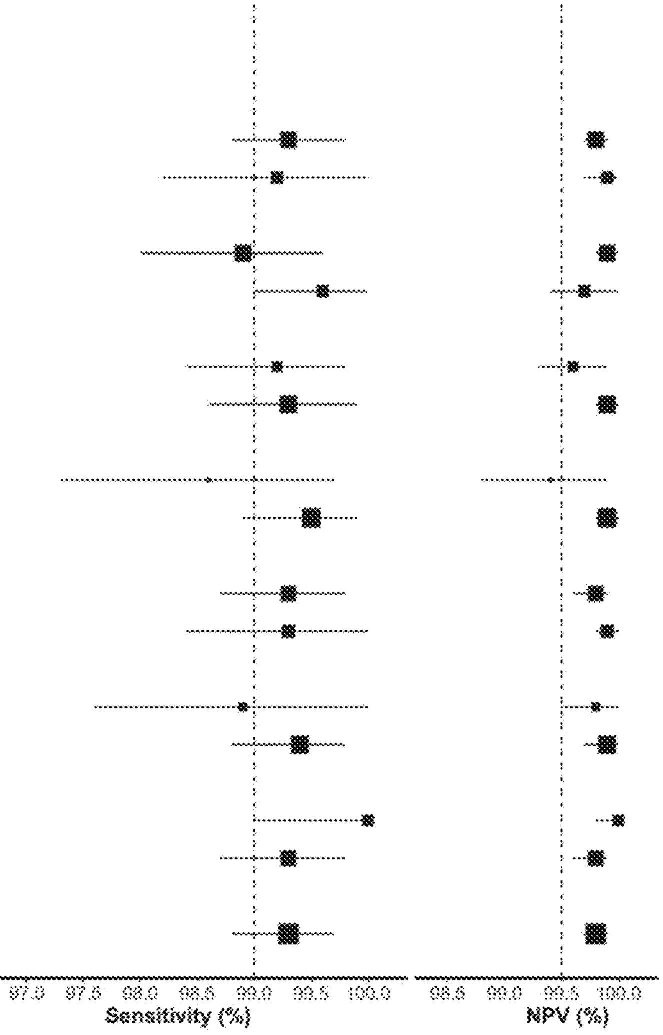
FIG. 9 shows subgroup performance to risk stratify to low-risk with a risk estimating index of <1.1.
Figure 10:
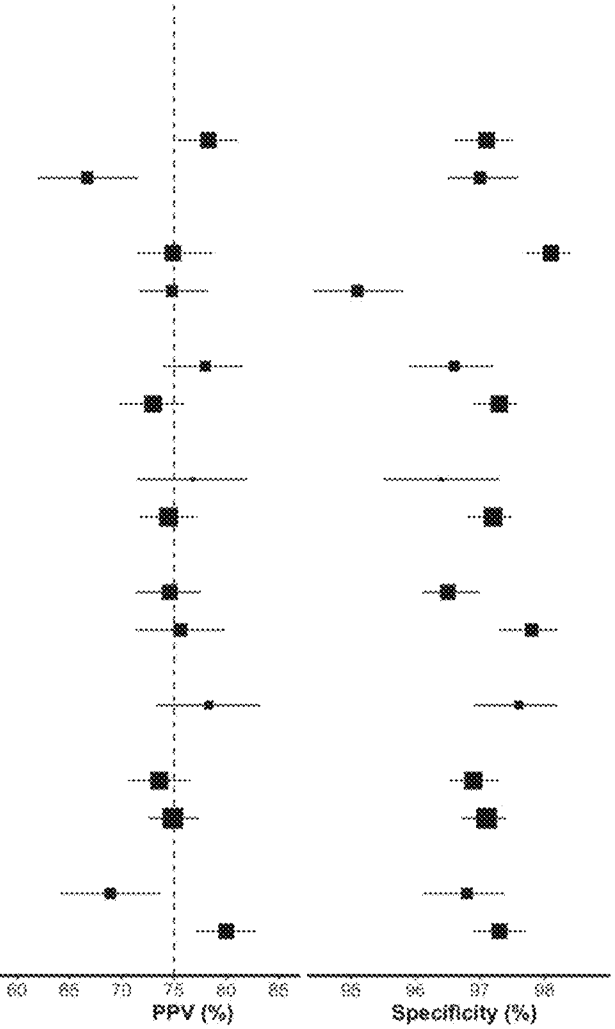
FIG. 10 shows subgroup performance to risk stratify to high-risk with a risk estimating index of ≥57.1.

The risk estimating index threshold of 1.1 performed similarly across all subgroups including in patients who presented early with symptoms for less than 3 hours (FIG. 9). The risk estimating index of 57.1 also performed similarly across most groups (FIG. 10) with the exception of Sex and Time from Symptom onset where the lower PPV for females compared to males, and for those with symptoms less than 3 h compared to those with symptoms more than 3 h, reflected lower prevalence.

Performance in Individual Cohorts

Figure 11:
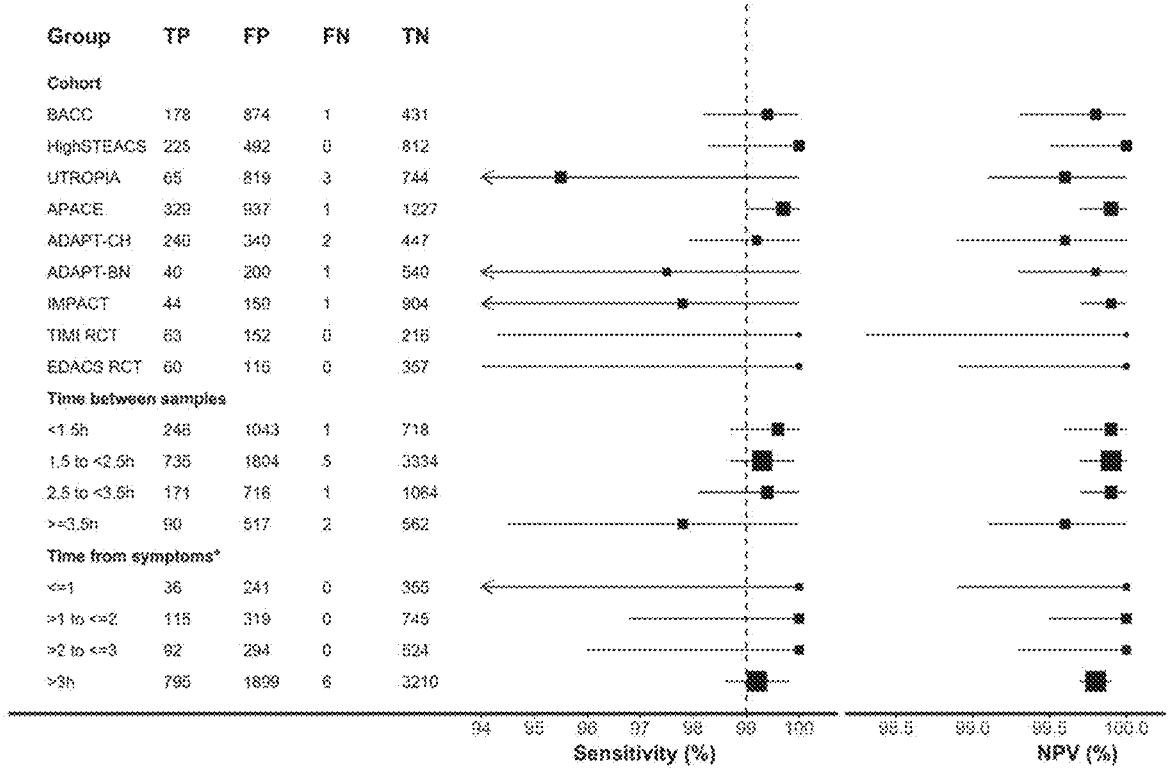
FIG. 11 shows a forest plot of the Sensitivity and NPV of an index value threshold of 1.1 for each cohorts and subgroups (in Example 4) of time between samples and time from symptoms to first blood sample. *Note: BACC cohort data was only available as a dichotomous variable for ≤3 h and >3 h so not included here.
Figure 12:
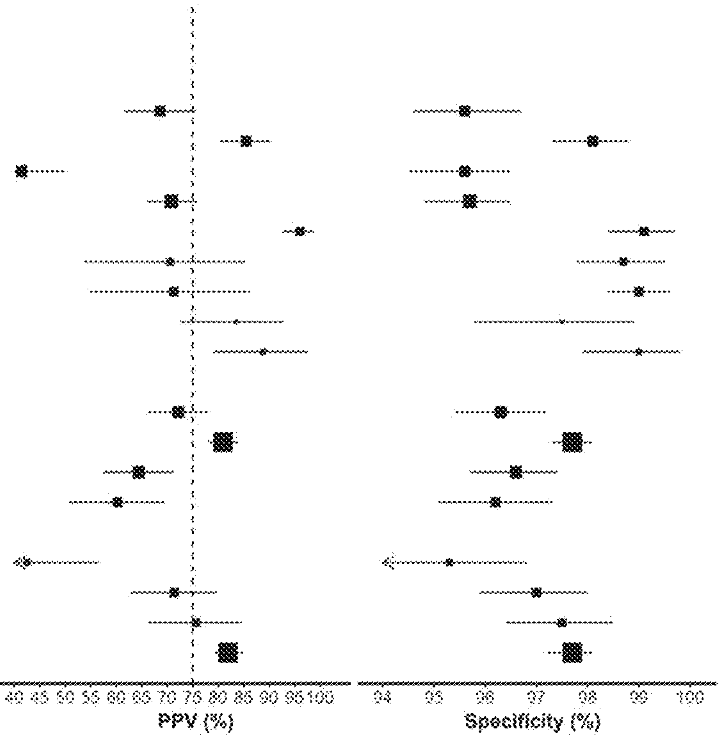
FIG. 12 shows a forest plot of the PPV and Specificity of an index value threshold of 57.1 for each cohorts and subgroups (in Example 4) of time between samples and time from symptoms to first blood sample. *Note: BACC cohort data was only available as a dichotomous variable for ≤3 h and >3 h so not included here.

At the MI3 index threshold of 1.1 between 43.7% and 82.3% of patients were classified as low-risk across individual cohorts. Sensitivity varied from 95.5% to 100% and NPV from 99.6% to 100% (FIG. 11). At the index threshold of 57.1 the PPV varied from 41.3% in the cohort (UTRO- PIA) with lowest prevalence to 96.1% in the cohort (ADAPT-CH) with greatest prevalence (FIGS. 11 and 12).

Further Sensitivity Analyses

The risk estimating index threshold of 1.1 performed well with high point estimates of sensitivity and NPV independently of time between samples and further stratification of time from symptoms to first blood draw (FIG. 11). The risk estimating index threshold of 57.1 exhibited increasing PPV and specificity with increasing time from symptom onset to first blood draw and possibly decreasing performance for increasing time between samples (FIG. 12).

Type 1 Myocardial Infarction within 30 Days

Including all patients with type 1 myocardial infarction within 30 days marginally resulted in a lower sensitivity of a risk estimating index at 1.1 of 99.1% (98.6 to 99.6%) and at 57.1 a similar PPV of 74.9% (72.3% to 77.2%).

Rapid Approach

Figure 13:
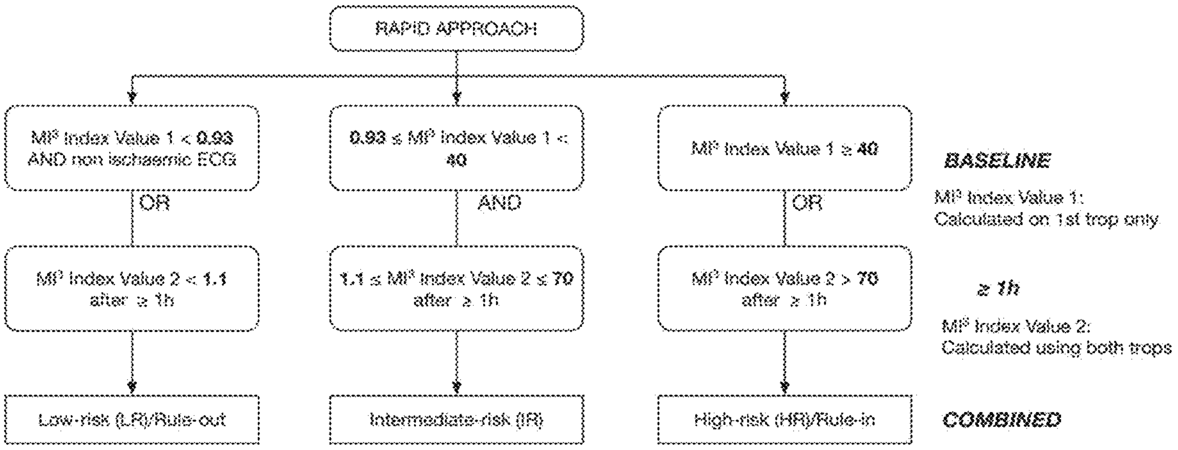
FIG. 13 shows a flow chart for estimating a patients' risk of type I myocardia infarction using one of the rapid approaches discussed in Example 4.

Baseline MI3 (calculated on initial troponin value only) provides a quick rule out without having to wait for a serial sample. This rules out a large proportion of the low risk patients. Baseline MI3 also stratifies the high risk individuals without having to wait for a serial sample. So the lowest and highest risk patients are triaged right away. Baseline MI3 does not utilize rate of rise calculation but only initial troponin result, age and gender. This approach is shown in FIG. 13.

Figure 14:
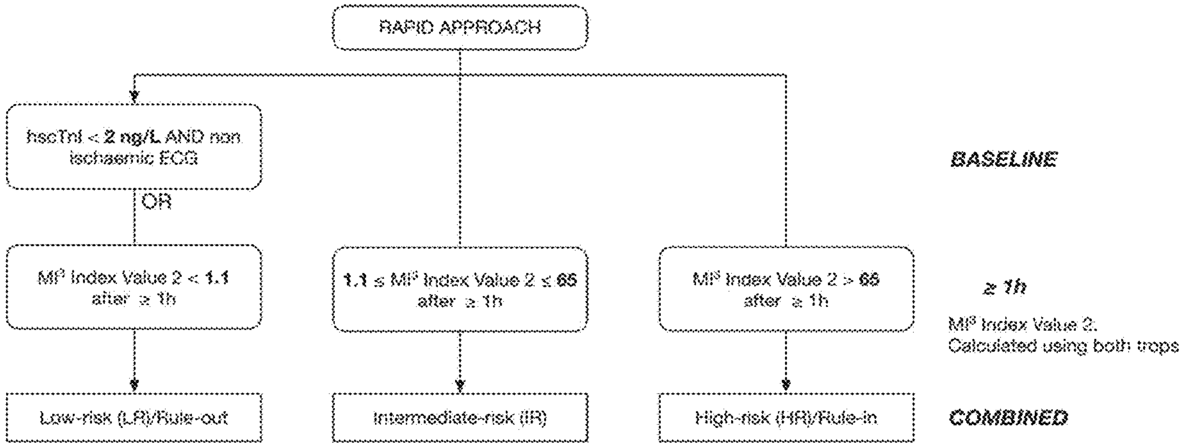
FIG. 14 shows a flow chart for estimating a patients' risk of type I myocardia infarction using one of the rapid approaches discussed in Example 4.

Another rapid approach, shown in FIG. 14, combines MI3 index calculation with a hsTnI concentration of <2 ng/L which is adds to the combined safety of ruling out very low risk patients. Combining a safe troponin concentration as well as a safe MI3 index insures only very low risk patients are omitted from further testing and follow-up for ischemic chest pain. Baseline MI3 index calculation does not utilize rate of rise calculation but only initial troponin result, age and gender.

Example 5

Risk Stratification of Patients of Suspected Myocardial Infarction Using Troponin T This example describes an exemplary method for employing troponin T (TnT) testing and algorithms to risk stratify patients of having myocardial infarction. There are 956 patients from BACC cohort with at least 2 Troponin T results that were included in the analysis. 341 (35.67) of them are females and 615 (64.33) are males. 179 out of 956 are adjudicated MI patients. The MI3 algorithm was then applied to the two first two available Troponin T values of these 956 patients and an index value were generated for each patient. Then Sensitivity, Specificity, NPV and PPV were calculated to each index value from 0 to 100 by the increment of 1.00. The 987 trees used for calculating the index value are shown in Appendix B. As with the above, TnI, the TnT index values were calculated with the following formulas:

$$\text{Sum Score: } SS = \left(\frac{1}{2}\right)\times\sum_{i=0}^{N=987}\text{score}_i + \left(\frac{1}{2}\right)\times\ln\frac{(1-0.727646454265159)}{(1+0.727646454265159)}$$

$$\text{Final Index: } IDX = \frac{1}{\left(1+\exp^{(-2\times SS)}\right)}\times 100$$

The numbers for each patient sample were plugged into the above formula in light of the 987 trees shown in Appendix B.

TABLE 10

INDEX REFERENCE TABLE

| Cutoff | Risk level | MI Pos | MI Neg | Non-MI Pos | Non-MI Neg | Sensitivity (%) [95% CI] | Specificity (%) [95% CI] | PPV (%) [95% CI] | NPV (%) [95% CI] |
|---|---|---|---|---|---|---|---|---|---|
| 0.00 | low | 179 | 0 | 777 | 0 | 100.00 [97.96, 100.00] | 0.00 [0.00, 0.47] | 18.72 [16.30, 21.34] | 100.00 [97.32, 100.00]* |
| 1.00 | low | 179 | 0 | 641 | 136 | 100.00 [97.96, 100.00] | 17.50 [14.89, 20.36] | 21.83 [19.05, 24.82] | 100.00 [97.32, 100.00] |
| 2.00 | Mod. | 177 | 2 | 351 | 426 | 98.88 [96.02, 99.86] | 54.83 [51.25, 58.37] | 33.52 [29.50, 37.73] | 99.53 [98.32, 99.94] |
| 3.00 | Mod. | 176 | 3 | 242 | 535 | 98.32 [95.18, 99.65] | 68.85 [65.47, 72.10] | 42.11 [37.32, 47.00] | 99.44 [98.38, 99.88] |
| 4.00 | Mod. | 171 | 8 | 187 | 590 | 95.53 [91.38, 98.05] | 75.93 [72.77, 78.90] | 47.77 [42.49, 53.08] | 98.66 [97.38, 99.42] |
| 5.00 | Mod. | 169 | 10 | 171 | 606 | 94.41 [89.97, 97.29] | 77.99 [74.91, 80.86] | 49.71 [44.27, 55.15] | 98.38 [97.03, 99.22] |
| 6.00 | Mod. | 168 | 11 | 168 | 609 | 93.85 [89.27, 96.89] | 78.38 [75.31, 81.23] | 50.00 [44.53, 55.47] | 98.23 [96.85, 99.11] |
| 7.00 | Mod. | 168 | 11 | 159 | 618 | 93.85 [89.27, 96.89] | 79.54 [76.53, 82.32] | 51.38 [45.81, 56.91] | 98.25 [96.89, 99.12] |
| 8.00 | Mod. | 163 | 16 | 149 | 628 | 91.06 [85.89, 94.80] | 80.82 [77.88, 83.53] | 52.24 [46.54, 57.90] | 97.52 [96.00, 98.57] |
| 9.00 | Mod. | 162 | 17 | 141 | 636 | 90.50 [85.23, 94.37] | 81.85 [78.96, 84.50] | 53.47 [47.67, 59.19] | 97.40 [95.86, 98.48] |
| 10.00 | Mod. | 161 | 18 | 118 | 659 | 89.94 [84.57, 93.93] | 84.81 [82.09, 87.27] | 57.71 [51.67, 63.57] | 97.34 [95.83, 98.42] |
| 11.00 | Mod. | 157 | 22 | 101 | 676 | 87.71 [81.99, 92.13] | 87.00 [84.43, 89.29] | 60.85 [54.61, 66.85] | 96.85 [95.27, 98.01] |
| 12.00 | Mod. | 155 | 24 | 86 | 691 | 86.59 [80.71, 91.22] | 88.93 [86.51, 91.05] | 64.32 [57.91, 70.36] | 96.64 [95.05, 97.84] |
| 13.00 | Mod. | 150 | 29 | 79 | 698 | 83.80 [77.57, 88.87] | 89.83 [87.49, 91.87] | 65.50 [58.96, 71.64] | 96.01 [94.32, 97.31] |
| 14.00 | Mod. | 148 | 31 | 79 | 698 | 82.68 [76.33, 87.92] | 89.83 [87.49, 91.87] | 65.20 [58.61, 71.38] | 95.75 [94.02, 97.09] |
| 15.00 | Mod. | 148 | 31 | 76 | 701 | 82.68 [76.33, 87.92] | 90.22 [87.91, 92.22] | 66.07 [59.47, 72.24] | 95.77 [94.04, 97.10] |
| 16.00 | Mod. | 148 | 31 | 74 | 703 | 82.68 [76.33, 87.92] | 90.48 [88.19, 92.45] | 66.67 [60.05, 72.83] | 95.78 [94.06, 97.11] |
| 17.00 | Mod. | 148 | 31 | 69 | 708 | 82.68 [76.33, 87.92] | 91.12 [88.90, 93.03] | 68.20 [61.56, 74.34] | 95.81 [94.10, 97.13] |
| 18.00 | Mod. | 146 | 33 | 68 | 709 | 81.56 [75.10, 86.96] | 91.25 [89.04, 93.14] | 68.22 [61.53, 74.40] | 95.55 [93.81, 96.92] |
| 19.00 | Mod. | 145 | 34 | 59 | 718 | 81.01 [74.48, 86.47] | 92.41 [90.31, 94.17] | 71.08 [64.34, 77.20] | 95.48 [93.74, 96.85] |
| 20.00 | Mod. | 143 | 36 | 55 | 722 | 79.89 [73.26, 85.50] | 92.92 [90.89, 94.62] | 72.22 [65.43, 78.34] | 95.25 [93.49, 96.65] |
| 21.00 | Mod. | 137 | 42 | 50 | 727 | 76.54 [69.64, 82.54] | 93.56 [91.60, 95.19] | 73.26 [66.31, 79.46] | 94.54 [92.69, 96.04] |
| 22.00 | Mod. | 134 | 45 | 47 | 730 | 74.86 [67.84, 81.03] | 93.95 [92.04, 95.52] | 74.03 [67.01, 80.25] | 94.19 [92.31, 95.73] |
| 23.00 | Mod. | 131 | 48 | 41 | 736 | 73.18 [66.06, 79.52] | 94.72 [92.91, 96.19] | 76.16 [69.08, 82.32] | 93.88 [91.96, 95.45] |
| 24.00 | Mod. | 129 | 50 | 34 | 743 | 72.07 [64.88, 78.50] | 95.62 [93.94, 96.95] | 79.14 [72.09, 85.10] | 93.69 [91.77, 95.28] |
| 25.00 | Mod. | 126 | 53 | 30 | 747 | 70.39 [63.12, 76.97] | 96.14 [94.53, 97.38] | 80.77 [73.70, 86.63] | 93.38 [91.42, 95.00] |
| 26.00 | Mod. | 120 | 59 | 26 | 751 | 67.04 [59.63, 73.87] | 96.65 [95.14, 97.80] | 82.19 [75.01, 88.02] | 92.72 [90.70, 94.41] |
| 27.00 | Mod. | 119 | 60 | 23 | 754 | 66.48 [59.06, 73.35] | 97.04 [95.59, 98.11] | 83.80 [76.69, 89.45] | 92.63 [90.61, 94.33] |
| 28.00 | Mod. | 117 | 62 | 23 | 754 | 65.36 [57.90, 72.30] | 97.04 [95.59, 98.11] | 83.57 [76.38, 89.29] | 92.40 [90.37, 94.13] |
| 29.00 | Mod. | 116 | 63 | 21 | 756 | 64.80 [57.33, 71.78] | 97.30 [95.90, 98.32] | 84.67 [77.53, 90.25] | 92.31 [90.27, 94.04] |
| 30.00 | Mod. | 111 | 68 | 20 | 757 | 62.01 [54.47, 69.15] | 97.43 [96.05, 98.42] | 84.73 [77.41, 90.42] | 91.76 [89.67, 93.54] |

TABLE 10-continued

INDEX REFERENCE TABLE

| Cutoff | Risk level | MI Pos | MI Neg | Non-MI Pos | Non-MI Neg | Sensitivity (%) [95% CI] | Specificity (%) [95% CI] | PPV (%) [95% CI] | NPV (%) [95% CI] |
|---|---|---|---|---|---|---|---|---|---|
| 31.00 | Mod. | 110 | 69 | 17 | 760 | 61.45 [53.90, 68.62] | 97.81 [96.52, 98.72] | 86.61 [79.44, 92.00] | 91.68 [89.58, 93.47] |
| 32.00 | Mod. | 109 | 70 | 17 | 760 | 60.89 [53.33, 68.09] | 97.81 [96.52, 98.72] | 86.51 [79.28, 91.94] | 91.57 [89.46, 93.37] |
| 33.00 | Mod. | 108 | 71 | 17 | 760 | 60.34 [52.77, 67.56] | 97.81 [96.52, 98.72] | 86.40 [79.12, 91.87] | 91.46 [89.34, 93.27] |
| 34.00 | Mod. | 106 | 73 | 16 | 761 | 59.22 [51.64, 66.49] | 97.94 [96.68, 98.82] | 86.89 [79.58, 92.31] | 91.25 [89.12, 93.08] |
| 35.00 | Mod. | 105 | 74 | 16 | 761 | 58.66 [51.07, 65.95] | 97.94 [96.68, 98.82] | 86.78 [79.42, 92.25] | 91.14 [89.00, 92.98] |
| 36.00 | Mod. | 104 | 75 | 15 | 762 | 58.10 [50.51, 65.42] | 98.07 [96.84, 98.92] | 87.39 [80.06, 92.77] | 91.04 [88.90, 92.89] |
| 37.00 | Mod. | 102 | 77 | 12 | 765 | 56.98 [49.39, 64.35] | 98.46 [97.32, 99.20] | 89.47 [82.33, 94.44] | 90.86 [88.70, 92.72] |
| 38.00 | Mod. | 101 | 78 | 12 | 765 | 56.42 [48.83, 63.81] | 98.46 [97.32, 99.20] | 89.38 [82.18, 94.39] | 90.75 [88.59, 92.62] |
| 39.00 | Mod. | 101 | 78 | 10 | 767 | 56.42 [48.83, 63.81] | 98.71 [97.65, 99.38] | 90.99 [84.06, 95.59] | 90.77 [88.61, 92.64] |
| 40.00 | Mod. | 101 | 78 | 9 | 768 | 56.42 [48.83, 63.81] | 98.84 [97.81, 99.47] | 91.82 [85.04, 96.19] | 90.78 [88.63, 92.64] |
| 41.00 | Mod. | 99 | 80 | 7 | 770 | 55.31 [47.71, 62.73] | 99.10 [98.15, 99.64] | 93.40 [86.87, 97.30] | 90.59 [88.42, 92.47] |
| 42.00 | Mod. | 98 | 81 | 7 | 770 | 54.75 [47.15, 62.19] | 99.10 [98.15, 99.64] | 93.33 [86.75, 97.28] | 90.48 [88.31, 92.37] |
| 43.00 | Mod. | 96 | 83 | 7 | 770 | 53.63 [46.04, 61.10] | 99.10 [98.15, 99.64] | 93.20 [86.50, 97.22] | 90.27 [88.08, 92.18] |
| 44.00 | Mod. | 96 | 83 | 7 | 770 | 53.63 [46.04, 61.10] | 99.10 [98.15, 99.64] | 93.20 [86.50, 97.22] | 90.27 [88.08, 92.18] |
| 45.00 | Mod. | 95 | 84 | 6 | 771 | 53.07 [45.48, 60.56] | 99.23 [98.33, 99.72] | 94.06 [87.52, 97.79] | 90.18 [87.98, 92.09] |
| 46.00 | Mod. | 95 | 84 | 6 | 771 | 53.07 [45.48, 60.56] | 99.23 [98.33, 99.72] | 94.06 [87.52, 97.79] | 90.18 [87.98, 92.09] |
| 47.00 | Mod. | 94 | 85 | 6 | 771 | 52.51 [44.93, 60.01] | 99.23 [98.33, 99.72] | 94.00 [87.40, 97.77] | 90.07 [87.87, 91.99] |
| 48.00 | Mod. | 94 | 85 | 5 | 772 | 52.51 [44.93, 60.01] | 99.36 [98.50, 99.79] | 94.95 [88.61, 98.34] | 90.08 [87.88, 92.00] |
| 49.00 | Mod. | 93 | 86 | 5 | 772 | 51.96 [44.38, 59.47] | 99.36 [98.50, 99.79] | 94.90 [88.49, 98.32] | 89.98 [87.77, 91.90] |
| 50.00 | Mod. | 92 | 87 | 5 | 772 | 51.40 [43.83, 58.92] | 99.36 [98.50, 99.79] | 94.85 [88.38, 98.31] | 89.87 [87.66, 91.81] |
| 51.00 | Mod. | 90 | 89 | 4 | 773 | 50.28 [42.72, 57.82] | 99.49 [98.69, 99.86] | 95.74 [89.46, 98.83] | 89.68 [87.45, 91.63] |
| 52.00 | Mod. | 85 | 94 | 4 | 773 | 47.49 [39.99, 55.07] | 99.49 [98.69, 99.86] | 95.51 [88.89, 98.76] | 89.16 [86.90, 91.15] |
| 53.00 | Mod. | 81 | 98 | 4 | 773 | 45.25 [37.81, 52.85] | 99.49 [98.69, 99.86] | 95.29 [88.39, 98.70] | 88.75 [86.46, 90.77] |
| 54.00 | Mod. | 79 | 100 | 4 | 773 | 44.13 [36.73, 51.73] | 99.49 [98.69, 99.86] | 95.18 [88.12, 98.67] | 88.55 [86.24, 90.58] |
| 55.00 | Mod. | 77 | 102 | 4 | 773 | 43.02 [35.65, 50.61] | 99.49 [98.69, 99.86] | 95.06 [87.84, 98.64] | 88.34 [86.03, 90.39] |
| 56.00 | Mod. | 76 | 103 | 4 | 773 | 42.46 [35.12, 50.05] | 99.49 [98.69, 99.86] | 95.00 [87.69, 98.62] | 88.24 [85.92, 90.30] |
| 57.00 | Mod. | 76 | 103 | 4 | 773 | 42.46 [35.12, 50.05] | 99.49 [98.69, 99.86] | 95.00 [87.69, 98.62] | 88.24 [85.92, 90.30] |
| 58.00 | high | 75 | 104 | 3 | 774 | 41.90 [34.58, 49.49] | 99.61 [98.88, 99.92] | 96.15 [89.17, 99.20] | 88.15 [85.83, 90.22] |
| 59.00 | high | 75 | 104 | 3 | 774 | 41.90 [34.58, 49.49] | 99.61 [98.88, 99.92] | 96.15 [89.17, 99.20] | 88.15 [85.83, 90.22] |
| 60.00 | high | 73 | 106 | 2 | 775 | 40.78 [33.51, 48.36] | 99.74 [99.07, 99.97] | 97.33 [90.70, 99.68] | 87.97 [85.64, 90.04] |
| 61.00 | high | 66 | 113 | 2 | 775 | 36.87 [29.80, 44.39] | 99.74 [99.07, 99.97] | 97.06 [89.78, 99.64] | 87.27 [84.90, 89.40] |
| 62.00 | high | 65 | 114 | 2 | 775 | 36.31 [29.27, 43.82] | 99.74 [99.07, 99.97] | 97.01 [89.63, 99.64] | 87.18 [84.80, 89.30] |
| 63.00 | high | 62 | 117 | 2 | 775 | 34.64 [27.70, 42.10] | 99.74 [99.07, 99.97] | 96.88 [89.16, 99.62] | 86.88 [84.49, 89.03] |
| 64.00 | high | 58 | 121 | 2 | 775 | 32.40 [25.61, 39.79] | 99.74 [99.07, 99.97] | 96.67 [88.47, 99.59] | 86.50 [84.08, 88.67] |
| 65.00 | high | 54 | 125 | 1 | 776 | 30.17 [23.54, 37.46] | 99.87 [99.29, 100.00] | 98.18 [90.28, 99.95] | 86.13 [83.70, 88.32] |
| 66.00 | high | 52 | 127 | 1 | 776 | 29.05 [22.52, 36.29] | 99.87 [99.29, 100.00] | 98.11 [89.93, 99.95] | 85.94 [83.50, 88.14] |
| 67.00 | high | 50 | 129 | 1 | 776 | 27.93 [21.50, 35.12] | 99.87 [99.29, 100.00] | 98.04 [89.55, 99.95] | 85.75 [83.30, 87.96] |
| 68.00 | high | 47 | 132 | 1 | 776 | 26.26 [19.97, 33.34] | 99.87 [99.29, 100.00] | 97.92 [88.93, 99.95] | 85.46 [83.00, 87.69] |
| 69.00 | high | 40 | 139 | 1 | 776 | 22.35 [16.47, 29.16] | 99.87 [99.29, 100.00] | 97.56 [87.14, 99.94] | 84.81 [82.32, 87.07] |
| 70.00 | high | 37 | 142 | 1 | 776 | 20.67 [14.99, 27.35] | 99.87 [99.29, 100.00] | 97.37 [86.19, 99.93] | 84.53 [82.03, 86.81] |
| 71.00 | high | 33 | 146 | 0 | 777 | 18.44 [13.04, 24.90] | 100.00 [99.53, 100.00] | 100.00 [89.42, 100.00] | 84.18 [81.67, 86.48] |
| 72.00 | high | 32 | 147 | 0 | 777 | 17.88 [12.56, 24.29] | 100.00 [99.53, 100.00] | 100.00 [89.11, 100.00] | 84.09 [81.57, 86.39] |
| 73.00 | high | 28 | 151 | 0 | 777 | 15.64 [10.65, 21.81] | 100.00 [99.53, 100.00] | 100.00 [87.66, 100.00] | 83.73 [81.19, 86.05] |
| 74.00 | high | 24 | 155 | 0 | 777 | 13.41 [8.78, 19.29] | 100.00 [99.53, 100.00] | 100.00 [85.75, 100.00] | 83.37 [80.82, 85.70] |
| 75.00 | high | 21 | 158 | 0 | 777 | 11.73 [7.41, 17.37] | 100.00 [99.53, 100.00] | 100.00 [83.89, 100.00] | 83.10 [80.54, 85.45] |
| 76.00 | high | 19 | 160 | 0 | 777 | 10.61 [6.51, 16.08] | 100.00 [99.53, 100.00] | 100.00 [82.35, 100.00] | 82.92 [80.36, 85.28] |
| 77.00 | high | 16 | 163 | 0 | 777 | 8.94 [5.20, 14.11] | 100.00 [99.53, 100.00] | 100.00 [79.41, 100.00] | 82.66 [80.08, 85.03] |
| 78.00 | high | 13 | 166 | 0 | 777 | 7.26 [3.92, 12.10] | 100.00 [99.53, 100.00] | 100.00 [75.29, 100.00] | 82.40 [79.81, 84.78] |
| 79.00 | high | 12 | 167 | 0 | 777 | 6.70 [3.51, 11.42] | 100.00 [99.53, 100.00] | 100.00 [73.54, 100.00] | 82.31 [79.72, 84.69] |
| 80.00 | high | 9 | 170 | 0 | 777 | 5.03 [2.32, 9.33] | 100.00 [99.53, 100.00] | 100.00 [66.37, 100.00] | 82.05 [79.45, 84.44] |
| 81.00 | high | 7 | 172 | 0 | 777 | 3.91 [1.59, 7.89] | 100.00 [99.53, 100.00] | 100.00 [59.04, 100.00] | 81.88 [79.27, 84.28] |
| 82.00 | high | 7 | 172 | 0 | 777 | 3.91 [1.59, 7.89] | 100.00 [99.53, 100.00] | 100.00 [59.04, 100.00] | 81.88 [79.27, 84.28] |
| 83.00 | high | 4 | 175 | 0 | 777 | 2.23 [0.61, 5.62] | 100.00 [99.53, 100.00] | 100.00 [39.76, 100.00] | 81.62 [79.01, 84.03] |
| 84.00 | high | 2 | 177 | 0 | 777 | 1.12 [0.14, 3.98] | 100.00 [99.53, 100.00] | 100.00 [15.81, 100.00] | 81.45 [78.83, 83.87] |
| 85.00 | high | 1 | 178 | 0 | 777 | 0.56 [0.01, 3.07] | 100.00 [99.53, 100.00] | 100.00 [2.50, 100.00] | 81.36 [78.74, 83.78] |
| 86.00 | high | 0 | 179 | 0 | 777 | 0.00 [0.00, 2.04] | 100.00 [99.53, 100.00] | 100.00 [2.50, 100.00]* | 81.28 [78.66, 83.70] |
| 87.00 | high | 0 | 179 | 0 | 777 | 0.00 [0.00, 2.04] | 100.00 [99.53, 100.00] | 100.00 [2.50, 100.00]* | 81.28 [78.66, 83.70] |
| 88.00 | high | 0 | 179 | 0 | 777 | 0.00 [0.00, 2.04] | 100.00 [99.53, 100.00] | 100.00 [2.50, 100.00]* | 81.28 [78.66, 83.70] |
| 89.00 | high | 0 | 179 | 0 | 777 | 0.00 [0.00, 2.04] | 100.00 [99.53, 100.00] | 100.00 [2.50, 100.00]* | 81.28 [78.66, 83.70] |
| 90.00 | high | 0 | 179 | 0 | 777 | 0.00 [0.00, 2.04] | 100.00 [99.53, 100.00] | 100.00 [2.50, 100.00]* | 81.28 [78.66, 83.70] |
| 91.00 | high | 0 | 179 | 0 | 777 | 0.00 [0.00, 2.04] | 100.00 [99.53, 100.00] | 100.00 [2.50, 100.00]* | 81.28 [78.66, 83.70] |
| 92.00 | high | 0 | 179 | 0 | 777 | 0.00 [0.00, 2.04] | 100.00 [99.53, 100.00] | 100.00 [2.50, 100.00]* | 81.28 [78.66, 83.70] |
| 93.00 | high | 0 | 179 | 0 | 777 | 0.00 [0.00, 2.04] | 100.00 [99.53, 100.00] | 100.00 [2.50, 100.00]* | 81.28 [78.66, 83.70] |
| 94.00 | high | 0 | 179 | 0 | 777 | 0.00 [0.00, 2.04] | 100.00 [99.53, 100.00] | 100.00 [2.50, 100.00]* | 81.28 [78.66, 83.70] |
| 95.00 | high | 0 | 179 | 0 | 777 | 0.00 [0.00, 2.04] | 100.00 [99.53, 100.00] | 100.00 [2.50, 100.00]* | 81.28 [78.66, 83.70] |
| 96.00 | high | 0 | 179 | 0 | 777 | 0.00 [0.00, 2.04] | 100.00 [99.53, 100.00] | 100.00 [2.50, 100.00]* | 81.28 [78.66, 83.70] |
| 97.00 | high | 0 | 179 | 0 | 777 | 0.00 [0.00, 2.04] | 100.00 [99.53, 100.00] | 100.00 [2.50, 100.00]* | 81.28 [78.66, 83.70] |
| 98.00 | high | 0 | 179 | 0 | 777 | 0.00 [0.00, 2.04] | 100.00 [99.53, 100.00] | 100.00 [2.50, 100.00]* | 81.28 [78.66, 83.70] |
| 99.00 | high | 0 | 179 | 0 | 777 | 0.00 [0.00, 2.04] | 100.00 [99.53, 100.00] | 100.00 [2.50, 100.00]* | 81.28 [78.66, 83.70] |
| 100.00 | high | 0 | 179 | 0 | 777 | 0.00 [0.00, 2.04] | 100.00 [99.53, 100.00] | 100.00 [2.50, 100.00]* | 81.28 [78.66, 83.70] |

The results of this example for TnT (which also included TnI using the same process) are shown in Appendix C, listed in order from lowest MI3 index value to highest MI3 index value. Using the index reference table (Table 10 above), the patients with an index value of less than 1.1 for TnT are considered low risk of myocardial infraction. Those between 1.1 and 57.0 are considered moderate risk for myocardial infarction. And, those patients 57.1 and above are high risk of myocardial infraction. Appendix C also provides TnI index values for these patients, as well as a comparison of the calculated index values using TnI with the calculated index values using TnT.

REFERENCES FOR EXAMPLE 4

1 Sandoval Y, Smith S W, Apple F S. Present and Future of Cardiac Troponin in Clinical Practice: A Paradigm Shift to High-Sensitivity Assays. Am J Med 2016; 129: 354-65.

2 Hollander J E, Than M P, Mueller C. State-of-the-Art Evaluation of Emergency Department Patients Presenting With Potential Acute Coronary Syndromes. Circulation 2016; 134: 547-64.

3 Apple F S, Sandoval Y, Jaffe A S, Ordonez-Llanos J, for the IFCC Task Force on Clinical Applications of Cardiac Bio-Markers. Cardiac Troponin Assays: Guide to Understanding Analytical Characteristics and Their Impact on Clinical Care. Clinical Chemistry 2016; published online October 10. DOI:10.1373/clinchem.2016.255109.

4 Thygesen K, Alpert J S, Jaffe A S, Simoons M L, Chaitman B R. ESC/ACCF/AHA/WHF Expert Consensus Document: Third universal definition of myocardial infarction. Circulation 2012; 126: 2020-35.

5 Roffi M, Patrono C, Collet J-P, et al. 2015 ESC Guidelines for the management of acute coronary syndromes in patients presenting without persistent ST-segment elevation: Task Force for the Management of Acute Coronary Syndromes in Patients Presenting without Persistent ST-Segment Elevation of the European Society of Cardiology (ESC). Eur Heart J 2016; 37: 267-315.

6 Body R, Carley S, McDowell G, et al. Rapid exclusion of acute myocardial infarction in patients with undetectable troponin using a high-sensitivity assay. JACC 2011; 58: 1332-9.

7 Rubini Gimenez M, Hoeller R, Reichlin T, et al. Rapid rule out of acute myocardial infarction using undetectable levels of high-sensitivity cardiac troponin. Int J Cardiol 2013; 168: 3896-901.

8 Bandstein N, Ljung R, Johansson M, Holzmann M J. Undetectable High-Sensitivity Cardiac Troponin T Level in the Emergency Department and Risk of Myocardial Infarction. JACC 2014; 63: 2569-78.

9 Shah A, Anand A, Sandoval Y, Lee K K, Smith S W. High-sensitivity cardiac troponin I at presentation in patients with suspected acute coronary syndrome: a cohort study. The Lancet 2016. DOI:10.1016/S0140-6736(15)00391-8.

10 Carlton E, Greenslade J, Cullen L, et al. Evaluation of High-Sensitivity Cardiac Troponin I Levels in Patients With Suspected Acute Coronary Syndrome. JAMA Cardiology 2016; 1: 405-12.

11 Thelin J, Melander O, Öhlin B. Early rule-out of acute coronary syndrome using undetectable levels of high sensitivity troponin T. European Heart Journal: Acute Cardiovascular Care 2015; 4: 403-9.

12 Body R, Mueller C, Giannitsis E, et al. The Use of Very Low Concentrations of High-sensitivity Troponin T to Rule Out Acute Myocardial Infarction Using a Single Blood Test. Acad Emerg Med 2016; 23: 1004-13.

13 Rubini Gimenez M, Twerenbold R, Jaeger C, et al. One-hour rule-in and rule-out of acute myocardial infarction using high-sensitivity cardiac troponin I. Am J Med 2015; 128: 861-4.

14 M D C M, M D E G, M D M C, et al. Multicenter Evaluation of a 0-Hour/1-Hour Algorithm in the Diagnosis of Myocardial Infarction With High-Sensitivity Cardiac Troponin T. Annals of Emergency Medicine 2016; 68: 76-87.e4.

15 Reichlin T, Schindler C, Drexler B, et al. One-hour rule-out and rule-in of acute myocardial infarction using high-sensitivity cardiac troponin T. Arch Intern Med 2012; 172: 1211-8.

16 Zhelev Z, Hyde C, Youngman E, et al. Diagnostic accuracy of single baseline measurement of Elecsys Troponin T high-sensitive assay for diagnosis of acute myocardial infarction in emergency department: systematic review and meta-analysis. BMJ 2015; 350: h15.

17 Pickering J W, Greenslade J H, Cullen L, et al. Validation of presentation and 3 h high-sensitivity troponin to rule-in and rule-out acute myocardial infarction. Heart 2016; 102: 1270-8.

18 Pickering J W, Greenslade J H, Cullen L, et al. Assessment of the European Society of Cardiology 0 Hour/1 Hour Algorithm to Rule Out and Rule In Acute Myocardial Infarction. Circulation 2016; 134: 1532-41.

19 Parsonage W A, Mueller C, Greenslade J H, et al. Validation of NICE diagnostic guidance for rule out of myocardial infarction using high-sensitivity troponin tests. Heart 2016; 102: 1279-86.

20 Friedman J, Hastie T, Tibshirani R. Additive logistic regression: a statistical view of boosting. The annals of statistics 2000; 28: 337-407.

21 Bossuyt P M, Reitsma J B, Bruns D E, et al. STARD 2015: An Updated List of Essential Items for Reporting Diagnostic Accuracy Studies. Clinical Chemistry 2015; 61: 1446-52.

22 Collins G S, Reitsma J B, Altman D G, Moons K G M. Transparent Reporting of a Multivariable Prediction Model for Individual Prognosis Or Diagnosis (TRIPOD): the TRIPOD statement. J Clin Epidemiol 2015; 68: 112-21.

23 Thygesen K, Alpert J S, White H D, on behalf of the Joint ESC/ACCF/AHA/WHF Task Force for the Redefinition of Myocardial Infarction. Universal definition of myocardial infarction. Circulation 2007; 116: 2634-53.

24 Neumann J T, Sörensen N A, Schwemer T, et al. Diagnosis of Myocardial Infarction Using a High-Sensitivity Troponin I 1-Hour Algorithm. JAMA Cardiology 2016; 1: 397.

25 Than M P, Cullen L, Aldous S, et al. 2-Hour accelerated diagnostic protocol to assess patients with chest pain symptoms using contemporary troponins as the only biomarker: the ADAPT trial. JACC 2012; 59: 2091-8.

26 Than M P, Aldous S, Lord S J, et al. A 2-hour diagnostic protocol for possible cardiac chest pain in the emergency department: a randomized clinical trial. JAMA Intern Med 2014; 174: 51-8.

27 Reichlin T, Hochholzer W, Bassetti S, et al. Early diagnosis of myocardial infarction with sensitive cardiac troponin assays. N Engl J Med 2009; 361: 858-67.

28 Than M P, Pickering J W, Aldous S J, et al. Effectiveness of EDACS Versus ADAPT Accelerated Diagnostic Pathways for Chest Pain: A Pragmatic Randomized Controlled Trial Embedded Within Practice. Annals of Emergency Medicine 2016; 68: 93-102.el.

29 Sandoval Y, Smith S W, Shah A S V, et al. Rapid Rule-Out of Acute Myocardial Injury Using a Single High-Sensitivity Cardiac Troponin I Measurement. Clinical Chemistry 2017; 63: 369-76.

30 Than M P, Herbert M, Flaws D, et al. What is an acceptable risk of major adverse cardiac event in chest pain patients soon after discharge from the Emergency Department?: a clinical survey. Int J Cardiol 2013; 166: 752-4.

31 R Core Team. R: A language and environment for statistical computing. http://www.R-project.org/.

ADDITIONAL REFERENCES

Bashore et al., J Am Coll Cardiol. 2012 Jun. 12; 59(24): 2221-305.

Pope et al., N Engl J Med. 2000 Apr. 20; 342(16):1163-70.

Roffi et al., Eur Heart J. 2015 Aug. 29.

Aw et al., Clin Chim Acta. 2013 Jun. 25; 422:26-8.

Apple et al., Clin Chem 2012; 58:1574-81.

Shah et al., BMJ. 2015 Jan. 21; 350:g7873.

Gimenez, The American Journal of Medicine, 128(8): 861-871, 2015.

Although only a few exemplary embodiments have been described in detail, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure.

We claim:

1. A method for reporting an estimated risk of acute coronary syndrome (ACS) in a subject suspected of having ACS, and performing an action based on said estimated risk of ACS, comprising:

a) obtaining subject values for said subject, wherein said subject is suspected of having ACS, and wherein said subject values comprise:

i) at least one of the following: subject gender value, a subject ECG classification, a subject hematology parameter value, and subject age value, ii) subject initial cardiac troponin I (cTnI) concentration from an initial sample from said subject, and iii) a first and/or second subsequent cTnI concentration from corresponding first and/or second subsequent samples from said subject;

b) processing said subject values with a processing system such that an estimated risk of ACS is determined for said subject, wherein said processing system comprises:

i) a computer processor, and ii) non-transitory computer memory comprising one or more computer programs and a database, wherein said one or more computer programs comprise: a rate of change algorithm and an additive tree algorithm, and wherein said database comprises at least 10 number of decision trees, wherein each individual decision tree comprises at least two pre-determined splitting variables and at least three pre-determined terminal node values, wherein said at least two pre-determined splitting variables are selected from the group consisting of: a threshold cTnI rate of change value, a threshold initial cTnI concentration value, and at least one of the following: a gender value, an ECG threshold classification, a hematology parameter threshold value, and an age threshold value, wherein said one or more computer programs, in conjunction with said computer processor, is/are configured to:

A) apply said rate of change algorithm to determine a subject cTnI rate of change value from at least two of: said subject initial cTnI concentration, said first subsequent cTnI concentration, and said second subsequent cTnI concentration, B) apply said subject cTnI rate of change value, said subject initial cTnI concentration, and at least one of the following: said subject gender value, said subject ECG classification, said subject hematology parameter value, and said age value; to said database to determine a terminal node value for each of said at least 10 number of decision trees, and C) apply said additive tree algorithm to: I) determine a combined value from M number of said terminal node values, and II) process said combined value to determine an estimated risk of ACS for said subject;

c) reporting said estimated risk of ACS for said subject determined by said processing system;

d) identifying said subject as having a high estimated risk of ACS; and e) performing an action on the subject identified as having a high estimated risk of ACS, wherein said action is at least one of the following:

1) Performing coronary catheterization on the subject;

2) Treating the subject with a cardiovascular (CVD) therapeutic, or 3) admitting the subject to a hospital.

2. The method of claim 1, wherein said obtaining subject values comprises receiving said subject values from a testing lab, from said subject, from an analytical testing system, and/or from a hand-held or point of care testing device.

3. The method of claim 2, wherein said processing system further comprises said analytical testing system and/or said hand-held or point of care testing device.

4. The method of claim 1, wherein said obtaining subject values comprises electronically receiving said subject values.

5. The method of claim 1, wherein said obtaining subject values comprises testing said initial sample, said first subsequent sample, and/or said second subsequent sample with a cTnI detection assay.

6. The method of claim 5, wherein said cTnI detection assay comprises a single molecule detection assay or a bead-based immunoassay.

7. The method of claim 1, wherein said ACS is selected from the group consisting of ST elevation myocardial infarction (STEMI), non ST elevation myocardial infarction (NSTEMI), unstable angina, Type I myocardial infraction, Type II myocardial infraction, chest pain, and chest pain presenting within three hours or less for medical care.

8. The method of claim 1, further comprising manually or automatically inputting said subject values into said processing system.

9. The method of claim 1, wherein said subject is a human.

10. The method of claim 1, wherein said subject is a human with chest pain.

11. The method of claim 1, wherein at least one subject value comprises subject gender.

12. The method of claim 1, wherein at least one subject value comprises subject age.

13. The method of claim 1, wherein said at least one of said subject gender, said subject ECG value, said subject hematology parameter value, or subject age comprises said subject age and subject gender.

14. The method of claim 1, wherein said initial sample from said subject comprises a blood, serum, or plasma sample.

15. The method of claim 1, wherein said initial sample is taken from said subject at an Emergency Room or urgent care clinic.

16. The method of claim 1, wherein said first and/or second subsequent samples comprise blood, serum, or plasma samples.

* * * * *